United States Patent
Yoon et al.

(10) Patent No.: US 12,371,686 B2
(45) Date of Patent: Jul. 29, 2025

(54) RIBULOSE-PHOSPHATE 3-EPIMERASE MOTIF HAVING LOW SIDE REACTIVITY AND ENZYME INCLUDING THE SAME

(71) Applicant: CJ CHEILJEDANG CORPORATION, Seoul (KR)

(72) Inventors: Sang Young Yoon, Seoul (KR); Byung-sam Son, Seoul (KR); Hyun Kug Cho, Seoul (KR); Hyun June Park, Seoul (KR); Seung Hwan Kim, Seoul (KR); Sungjae Yang, Seoul (KR); Il Hyang Park, Seoul (KR); Seong Bo Kim, Seoul (KR)

(73) Assignee: CJ CHEILJEDANG CORPORATION

( * ) Notice: Subject to any disclaimer, the term of this patent is extended or adjusted under 35 U.S.C. 154(b) by 658 days.

(21) Appl. No.: 17/612,970

(22) PCT Filed: Apr. 29, 2020

(86) PCT No.: PCT/KR2020/005701
§ 371 (c)(1),
(2) Date: Nov. 19, 2021

(87) PCT Pub. No.: WO2020/235830
PCT Pub. Date: Nov. 26, 2020

(65) Prior Publication Data
US 2023/0051519 A1    Feb. 16, 2023

(30) Foreign Application Priority Data
May 21, 2019   (KR) .................. 10-2019-0059697

(51) Int. Cl.
C12N 9/90     (2006.01)
C12P 19/02    (2006.01)
C12P 19/24    (2006.01)

(52) U.S. Cl.
CPC .............. *C12N 9/90* (2013.01); *C12P 19/02* (2013.01); *C12P 19/24* (2013.01); *C12Y 501/03001* (2013.01)

(58) Field of Classification Search
CPC .............. C12Y 501/03001; C12N 9/90; C12P 19/02; C12P 19/24
See application file for complete search history.

(56) References Cited

U.S. PATENT DOCUMENTS

2016/0060635 A1   3/2016  Liao et al.
2019/0376101 A1*  12/2019 Wichelecki .... C12Y 204/01008

FOREIGN PATENT DOCUMENTS

| EP | 3663397 A2 | 6/2020 |
|---|---|---|
| KR | 10-2018-0004023 A | 1/2018 |
| KR | 10-1965509 B1 | 4/2019 |
| KR | 10-2080886 B1 | 2/2020 |
| WO | 03/084986 A2 | 10/2003 |
| WO | 2004/042043 A2 | 5/2004 |
| WO | 2018/112139 A1 | 6/2018 |
| WO | 2018/129275 A1 | 7/2018 |
| WO | 2018/132871 A1 | 7/2018 |

OTHER PUBLICATIONS

Baker, Brett J., et al. "Genomic resolution of linkages in carbon, nitrogen, and sulfur cycling among widespread estuary sediment bacteria." Microbiome 3 (2015): 1-12. (Year: 2015).*
Sikorski, Johannes, et al. "Complete genome sequence of Mahella australiensis type strain (50-1 BON T)." Standards in Genomic Sciences 4 (2011): 331-341. (Year: 2011).*
Ribulose Phosphate. Retrieved from https://www.ebi.ac.uk/QuickGO/term/GO:0004750 on Aug. 27, 24. (Year: 2024).*
Chan et al., "Structural Basis for Substrate Specificity in Phosphate Binding (beta/alpha)8-Barrels: D-Allulose 6-Phosphate 3-Epimerase from *Escherichia coli* K-12," Biochemistry, 47: 9608-9617 (2008).
Extended European Search Report issued in related European Patent Application No. 20809298.1 dated Apr. 12, 2022.
NCBI, GenBank Accession No. WP_093231204.1, 'ribulose-phosphate 3-epimerase [Thermoflavimicrobium dichotomicum]', Aug. 1, 2017.
Mu et al., "Recent advances on applications and biotechnological production of D-psicose," Applied Microbiology Biotechnology,94(6):1461-1467(2012).
Kim et. al., "Crystal Structure of d-Psicose 3-epimerase from Agrobacterium tumefaciens and its Complex with True Substrate d-Fructose," Journal of Molecular Biology, 361 (5): 920-931 (2006).
International Search Report issued in corresponding International Patent Application No. PCT/KR2020/005701 dated Aug. 10, 2020.

* cited by examiner

*Primary Examiner* — Robert J Yamasaki
*Assistant Examiner* — Trevor Kane
(74) *Attorney, Agent, or Firm* — Morgan, Lewis & Bockius LLP

(57) ABSTRACT

Provided are ribulose-phosphate 3-epimerase, a microorganism and a composition, each including the ribulose-phosphate 3-epimerase, and a method of producing psicose-6-phosphate or psicose using the same.

20 Claims, 2 Drawing Sheets

Specification includes a Sequence Listing.

[FIG. 1]
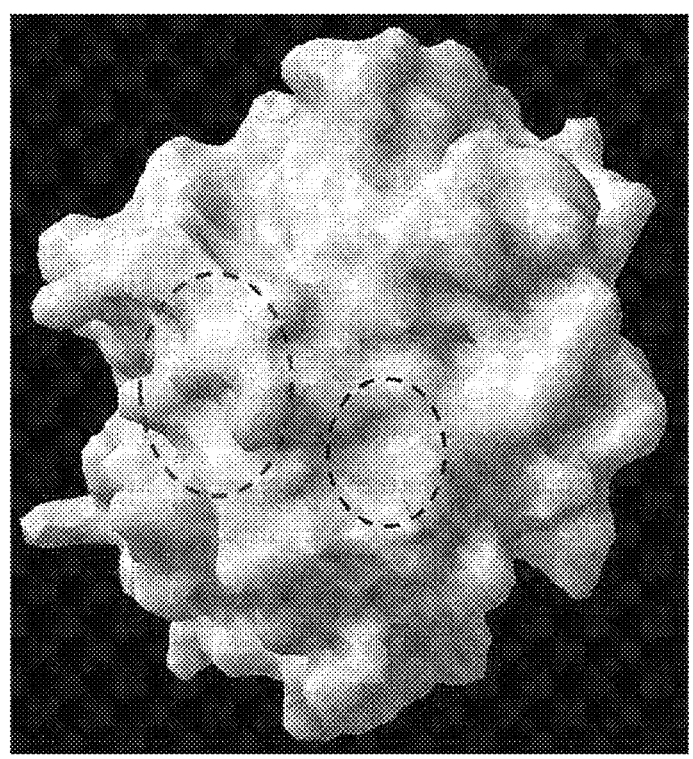

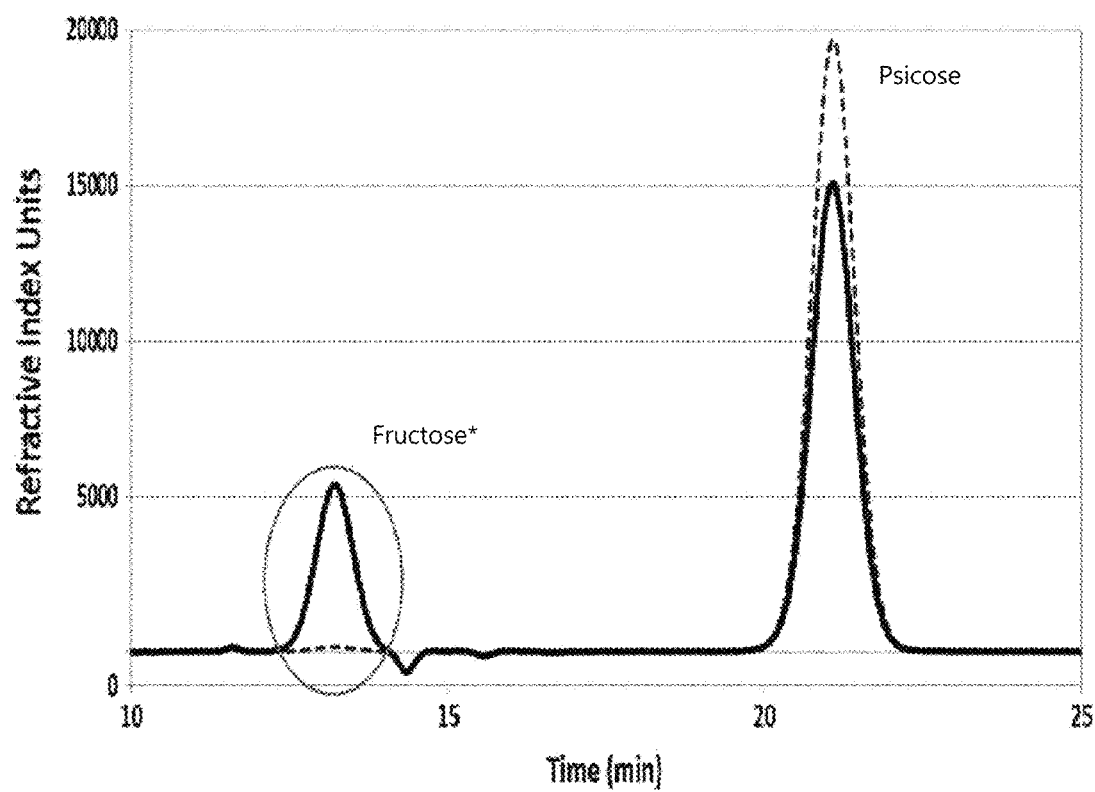
[FIG. 2]

SEQUENCE LISTING

<160> NUMBER OF SEQ ID NOS: 42

<210> SEQ ID NO 1
<211> LENGTH: 3
<212> TYPE: PRT
<213> ORGANISM: Artificial Sequence
<220> FEATURE:
<223> OTHER INFORMATION: Motif I

```
<400> SEQUENCE: 1

Val Asp Gly
1

<210> SEQ ID NO 2
<211> LENGTH: 6
<212> TYPE: PRT
<213> ORGANISM: Artificial Sequence
<220> FEATURE:
<223> OTHER INFORMATION: Motif II
<220> FEATURE:
<221> NAME/KEY: MISC_FEATURE
<222> LOCATION: (2)..(3)
<223> OTHER INFORMATION: Xaa=any amino acid

<400> SEQUENCE: 2

Met Xaa Xaa Asp Pro Gly
1               5

<210> SEQ ID NO 3
<211> LENGTH: 6
<212> TYPE: PRT
<213> ORGANISM: Artificial Sequence
<220> FEATURE:
<223> OTHER INFORMATION: Motif III
<220> FEATURE:
<221> NAME/KEY: MISC_FEATURE
<222> LOCATION: (2)..(3)
<223> OTHER INFORMATION: Xaa=any amino acid
<220> FEATURE:
<221> NAME/KEY: MISC_FEATURE
<222> LOCATION: (4)..(4)
<223> OTHER INFORMATION: Xaa=any amino acid except Asp

<400> SEQUENCE: 3

Met Xaa Xaa Xaa Pro Gly
1               5

<210> SEQ ID NO 4
<211> LENGTH: 4
<212> TYPE: PRT
<213> ORGANISM: Artificial Sequence
<220> FEATURE:
<223> OTHER INFORMATION: Motif
<220> FEATURE:
<221> NAME/KEY: MISC_FEATURE
<222> LOCATION: (2)..(2)
<223> OTHER INFORMATION: Xaa=any amino acid
<220> FEATURE:
<221> NAME/KEY: MISC_FEATURE
<222> LOCATION: (3)..(3)
<223> OTHER INFORMATION: Xaa=Met or Ile

<400> SEQUENCE: 4

Ser Xaa Xaa Cys
1

<210> SEQ ID NO 5
<211> LENGTH: 6
<212> TYPE: PRT
<213> ORGANISM: Artificial Sequence
<220> FEATURE:
<223> OTHER INFORMATION: Motif
<220> FEATURE:
<221> NAME/KEY: MISC_FEATURE
<222> LOCATION: (2)..(5)
<223> OTHER INFORMATION: Xaa=any amino acid
<220> FEATURE:
<221> NAME/KEY: MISC_FEATURE
<222> LOCATION: (6)..(6)
<223> OTHER INFORMATION: X=Phe or Leu
```

<400> SEQUENCE: 5

Gly Xaa Xaa Xaa Xaa
1               5

<210> SEQ ID NO 6
<211> LENGTH: 221
<212> TYPE: PRT
<213> ORGANISM: Thermoanaerobacterium thermosaccharolyticum

<400> SEQUENCE: 6

```
Met Lys Tyr Leu Phe Ser Pro Ser Leu Met Cys Met Asn Leu Ile Lys
1               5                   10                  15

Leu Asn Glu Gln Ile Ser Val Leu Asn Ser Lys Ala Asp Phe Leu His
            20                  25                  30

Val Asp Ile Met Asp Gly His Phe Val Lys Asn Ile Thr Leu Ser Pro
        35                  40                  45

Phe Phe Ile Glu Gln Ile Lys Ser Tyr Val Asn Ile Pro Ile Asp Ala
    50                  55                  60

His Leu Met Val Glu Asn Pro Gly Asp Tyr Ile Glu Ile Cys Glu Lys
65                  70                  75                  80

Ser Gly Ala Ser Phe Ile Thr Ile His Ala Glu Thr Ile Asn Arg Glu
                85                  90                  95

Ala Phe Arg Ile Ile Asp Arg Ile Lys Ser His Gly Leu Met Val Gly
            100                 105                 110

Ile Ala Leu Asn Pro Ala Thr Pro Ile Ser Glu Ile Lys His Tyr Ile
        115                 120                 125

Asn Lys Ile Asp Lys Ile Thr Ile Met Thr Val Asp Pro Gly Phe Ala
    130                 135                 140

Gly Gln Pro Phe Ile Pro Glu Val Leu Glu Lys Ile Arg Asp Leu Lys
145                 150                 155                 160

Arg Leu Lys Asp Asp Asn Asn Tyr Asn Tyr Leu Ile Glu Ala Asp Gly
                165                 170                 175

Ser Cys Asn Lys Asn Thr Phe Gln Val Leu Lys Asp Ala Gly Cys Lys
            180                 185                 190

Val Phe Val Leu Gly Ser Ser Gly Leu Phe Asn Leu Ser Asp Asp Leu
        195                 200                 205

Gly Lys Ala Trp Glu Ile Met Ile Gly Asn Phe Asn Gly
    210                 215                 220
```

<210> SEQ ID NO 7
<211> LENGTH: 230
<212> TYPE: PRT
<213> ORGANISM: Unknown
<220> FEATURE:
<223> OTHER INFORMATION: Bacillus thermoamylovorans

<400> SEQUENCE: 7

```
Met Ser Asn Lys Ile Glu Phe Ser Pro Ser Leu Met Thr Met Asp Leu
1               5                   10                  15

Asp Lys Phe Lys Glu Gln Ile Thr Phe Leu Asn Asn His Val Gly Ser
            20                  25                  30

Tyr His Ile Asp Ile Met Asp Gly His Tyr Val Pro Asn Ile Thr Leu
        35                  40                  45

Ser Pro Trp Phe Val Gln Glu Val Arg Lys Ile Ser Asp Val Pro Met
    50                  55                  60
```

Ser Ala His Leu Met Val Thr Asn Pro Ser Phe Trp Val Gln Gln Leu
65                  70                  75                  80

Ile Asp Ile Lys Cys Glu Trp Ile Cys Met His Val Glu Thr Leu Asp
                85                  90                  95

Gly Leu Ala Phe Arg Leu Ile Asp Gln Ile His Asp Ala Gly Leu Lys
            100                 105                 110

Ala Gly Val Val Leu Asn Pro Glu Thr Ser Val Asp Ala Ile Arg Pro
        115                 120                 125

Tyr Ile Asp Leu Val Asp Lys Val Thr Ile Met Thr Val Asp Pro Gly
130                 135                 140

Phe Ala Gly Gln Arg Phe Ile Asp Ser Thr Leu Glu Lys Ile Val Glu
145                 150                 155                 160

Leu Arg Lys Leu Arg Glu Glu His Gly Tyr Lys Tyr Val Ile Glu Met
                165                 170                 175

Asp Gly Ser Ser Asn Arg Lys Ser Phe Lys Lys Ile Tyr Glu Ala Gly
            180                 185                 190

Pro Asp Ile Tyr Ile Ile Gly Arg Ser Gly Leu Phe Gly Leu His Glu
        195                 200                 205

Asp Ile Glu Lys Ala Trp Glu Ile Met Cys Lys Asp Phe Glu Glu Met
210                 215                 220

Thr Gly Glu Lys Val Leu
225                 230

<210> SEQ ID NO 8
<211> LENGTH: 228
<212> TYPE: PRT
<213> ORGANISM: Brevibacillus thermoruber

<400> SEQUENCE: 8

Met Gly Phe Lys Phe Ser Pro Ser Leu Met Cys Met Asn Leu Leu Asp
1               5                   10                  15

Ile Gln His Gln Ile Glu Val Met Asn Arg Arg Ala Asp Leu Val His
            20                  25                  30

Ile Asp Ile Met Asp Gly His Tyr Val Lys Asn Leu Thr Leu Ser Pro
        35                  40                  45

Phe Phe Ile Glu Gln Leu Lys Glu Ser Leu His Val Pro Met Asp Val
    50                  55                  60

His Leu Met Val Glu Asn Pro Thr Asp Phe Ile Glu Arg Val Lys Glu
65                  70                  75                  80

Ala Gly Ala Ser Ile Ile Ser Pro His Ala Glu Thr Ile Asn Thr Asp
                85                  90                  95

Ala Phe Arg Ile Ile Asp Lys Val Lys Ser Leu Gly Cys Gln Met Gly
            100                 105                 110

Ile Val Leu Asn Pro Ala Thr Pro Ile Ala Tyr Ile Gln His Tyr Ile
        115                 120                 125

His Leu Val Asp Lys Ile Thr Ile Met Thr Val Asp Pro Gly Tyr Ala
130                 135                 140

Gly Gln Lys Phe Ile Pro Glu Met Leu Glu Lys Ile Arg Gln Ala Lys
145                 150                 155                 160

Arg Leu Lys Glu Glu Arg Gly Tyr Arg Tyr Leu Ile Glu Val Asp Gly
                165                 170                 175

Ser Cys Asn Val Gly Thr Phe Lys Arg Leu Ala Glu Ala Gly Ala Glu
            180                 185                 190

Val Phe Ile Val Gly Ser Ser Gly Leu Phe Asn Leu His Pro Asp Leu
        195                 200                 205

Glu Val Ala Trp Asp Met Met Met Asp Asn Phe Gln Arg Glu Val Gly
210                 215                 220

Glu Thr Thr Ala
225

<210> SEQ ID NO 9
<211> LENGTH: 227
<212> TYPE: PRT
<213> ORGANISM: Unknown
<220> FEATURE:
<223> OTHER INFORMATION: Anaerolineae bacterium SM23_84

<400> SEQUENCE: 9

Met Ile Lys Val Ala Pro Ser Ile Met Cys Ala Asp Leu Thr Cys Leu
1               5                   10                  15

Gly Asp Gln Val Gln Ala Leu Glu Gln Ala Gly Ala Asp Leu Phe His
            20                  25                  30

Phe Asp Ile Met Asp Gly His Phe Val Glu Asn Phe Thr Leu Ser Pro
        35                  40                  45

Thr Ile Leu Ala Ala Ile Arg Glu Leu Thr Val Val Pro Ile Glu Ala
    50                  55                  60

His Leu Met Ile Ser Glu Pro Arg Arg Tyr Leu Gln Met Cys Ala Asp
65                  70                  75                  80

Ala Gly Ala Asn Ile Ile Thr Val His Val Glu Val Cys Pro Arg Pro
                85                  90                  95

Tyr Gln Val Leu Ala Lys Ile Lys Asp Leu Gly Cys Val Pro Ala Leu
            100                 105                 110

Ala Leu Asn Pro Ala Thr Pro Leu Cys Phe Leu Asp Tyr Val Leu Gln
        115                 120                 125

Glu Ala Gly Ile Val Val Ile Met Thr Val Asp Pro Gly Phe Ala Gly
    130                 135                 140

Gln Glu Phe Ile Ala Ala Thr Leu Pro Lys Ile Arg Glu Leu Arg Glu
145                 150                 155                 160

Arg Ile Asp Gln Leu Asn Leu Asp Val Glu Ile Gln Val Asp Gly His
                165                 170                 175

Ile Asn Arg Glu Thr Ile Pro Leu Val Val Glu Ala Gly Ala Asp Ile
            180                 185                 190

Leu Val Leu Gly Thr Ser Gly Leu Phe Ser Leu Pro Gly Thr Leu Arg
        195                 200                 205

Glu Asn Ile Glu Ala Val Lys Gln Gln Ala Ala Ser Leu Leu Glu Arg
    210                 215                 220

Gln Lys Gly
225

<210> SEQ ID NO 10
<211> LENGTH: 226
<212> TYPE: PRT
<213> ORGANISM: Unknown
<220> FEATURE:
<223> OTHER INFORMATION: Petrotoga sp. 9T1HF07.CasAA.8.2

<400> SEQUENCE: 10

Met Ser Ile Leu Phe Ser Ala Ser Val Met Cys Ala Asp Phe Thr Asp
1               5                   10                  15

```
Leu Lys Asn Gln Leu Lys Lys Leu Glu Glu Ile Gly Ile His Arg Leu
             20                  25                  30

His Tyr Asp Ile Met Asp Gly Ile Phe Val Pro Asn Ile Thr Leu Gly
         35                  40                  45

Ile Asp Met Ile Arg Asp Ile Thr Lys Val Cys Ser Leu Pro Ile Asp
 50                  55                  60

Val His Leu Met Val Thr Glu Pro Ala Asn Phe Leu Glu Met Leu Ile
 65                  70                  75                  80

Lys Tyr Lys Ile Asp Ser Ile Ser Phe His Val Glu Ser Asn Pro Asn
                 85                  90                  95

Glu Ala Phe Arg Met Val Asp Trp Leu His Asp His Asn Ile Lys Ala
            100                 105                 110

Gly Ile Ala Ile Ser Pro Ile Thr Pro Val Ser Gln Ile Glu Leu Ile
        115                 120                 125

Leu Gly Arg Val Asp Ile Ile Thr Val Met Thr Val Asp Pro Gly Phe
130                 135                 140

Ala Gly Gln His Phe Ile Pro Val Val Leu Lys Lys Ile Asp Ala Leu
145                 150                 155                 160

Arg Lys Ile Arg Glu Glu Asn Asn Phe Lys Tyr Thr Ile Met Val Asp
                165                 170                 175

Gly Ser Val Asn Leu Lys Thr Ile Pro Glu Ile Met Thr His Ser Pro
            180                 185                 190

Asp Ile Leu Ile Leu Gly Asn Ser Gly Leu Phe Gly Asp Ser Glu Gly
        195                 200                 205

Leu Glu Ala Ala Tyr Lys Lys Ile Leu Thr Leu Pro Glu Val Lys Thr
210                 215                 220

Ser Leu
225

<210> SEQ ID NO 11
<211> LENGTH: 229
<212> TYPE: PRT
<213> ORGANISM: Unknown
<220> FEATURE:
<223> OTHER INFORMATION: Petrotoga sp. 9PWA.NaAc.5.4

<400> SEQUENCE: 11

Met Ser Leu Leu Phe Ser Ala Ser Val Met Cys Met Asp Phe Ser Asn
 1               5                  10                  15

Leu Ser Asn Gln Leu Lys Glu Ile Glu Glu Ile Gly Ile Asn Arg Leu
             20                  25                  30

His Tyr Asp Ile Met Asp Gly Lys Phe Val Pro Asn Ile Thr Leu Gly
         35                  40                  45

Phe Asp Met Ile Lys Asp Ile Thr Lys Ile Ser Thr Leu Pro Ile Asp
 50                  55                  60

Val His Leu Met Ile Glu Asn Pro Ser Lys Phe Ile Asn Ile Leu Lys
 65                  70                  75                  80

Asn Tyr Gln Val Asp Ser Ile Thr Phe His Val Glu Asn Thr Ile Asn
                 85                  90                  95

Glu Ala Phe Arg Ile Val Glu Leu Ile His Asn Asn Ile Lys Ala
            100                 105                 110

Gly Ile Ala Leu Ser Pro Leu Thr Pro Ile Thr Leu Ile Glu Leu Ile
        115                 120                 125

Leu Gly Arg Leu Asp Phe Ile Thr Ile Met Thr Val Asp Pro Gly Phe
130                 135                 140
```

Ala Gly Gln Gln Phe Ile Pro Glu Thr Leu Lys Lys Ile Asp Phe Leu
145                 150                 155                 160

Arg Asn Val Lys Glu Lys Asn Asn Tyr Ser Tyr Ser Ile Met Ile Asp
                165                 170                 175

Gly Ser Val Asn Leu Lys Thr Leu Pro Thr Ile Met Lys His Leu Pro
            180                 185                 190

Asp Ile Leu Ile Leu Gly Asn Ser Gly Leu Phe Gly Asn Pro Glu Gly
                195                 200                 205

Leu Lys Ala Thr Phe Tyr Lys Ile Thr Asn Ile Pro Glu Val Lys Asn
        210                 215                 220

Asn Tyr Gly Ala Lys
225

<210> SEQ ID NO 12
<211> LENGTH: 234
<212> TYPE: PRT
<213> ORGANISM: Artificial Sequence
<220> FEATURE:
<223> OTHER INFORMATION: ribulose-phosphate 3-epimerase

<400> SEQUENCE: 12

Met Thr Val Arg Val Ala Pro Ser Met Met Cys Ala Asp Gln Ala His
1               5                   10                  15

Leu Ala Asp Glu Val Arg Glu Leu Glu Met Leu Gly Val Asp Trp Leu
                20                  25                  30

His Met Asp Ile Met Asp Thr His Phe Val Pro Asn Met Pro Leu Gly
            35                  40                  45

Leu Thr Thr Val Glu His Leu Arg Ser Leu Thr Arg Leu Pro Phe Asp
        50                  55                  60

Val His Leu Met Val Glu His Asn Glu Leu Phe Ile Glu Arg Leu Ala
65                  70                  75                  80

Lys Ile Gly Val Gln Ser Ile Ser Val His Ala Glu Ser Thr Arg His
                85                  90                  95

Leu Asp Arg Val Leu Ser Leu Ile Arg Ala His Gly Ile Gln Ala Gly
            100                 105                 110

Val Ala Leu Asn Pro Ala Thr Pro Leu Ser Ala Leu Glu Tyr Val Arg
        115                 120                 125

Glu Leu Ile Asp Phe Val Leu Ile Met Thr Val Asn Pro Gly Phe Ala
    130                 135                 140

Gly Gln Leu Leu Thr Ala Ser Ala Ile Arg Lys Ile Glu Asp Cys Arg
145                 150                 155                 160

Arg Trp Leu Asp Glu Arg Gly Leu Ser Gln Leu Pro Ile Gln Val Asp
                165                 170                 175

Gly Asn Val Ser Phe Thr Asn Ile Ala Arg Met Val Ala Ala Gly Ala
            180                 185                 190

Asp Ile Leu Val Val Gly Ser Ser Ser Leu Phe Ala Ser Glu Arg Pro
        195                 200                 205

Arg Leu Glu Asn Met Arg Arg Ile Glu Gln Ala Ile Glu Glu Gly Met
    210                 215                 220

Arg Leu Arg Gln Glu Arg Ser Arg Lys Pro
225                 230

<210> SEQ ID NO 13
<211> LENGTH: 220
<212> TYPE: PRT
<213> ORGANISM: Thermoanaerobacter thermohydrosulfuricus

<400> SEQUENCE: 13

Met Ile Lys Ile Cys Pro Ser Leu Met Cys Ala Asp Phe Thr Lys Leu
1               5                   10                  15

Lys Glu Glu Ile Leu Glu Leu Glu Ser Ala Gly Ala Asp Met Phe His
                20                  25                  30

Leu Asp Ile Met Asp Gly Asn Phe Val Pro Asn Phe Ala Leu Gly Leu
            35                  40                  45

Glu Asp Val Lys Ala Val Ser Lys Ile Thr Ser Ile Pro Tyr Asp Val
    50                  55                  60

His Leu Met Ile Asn Glu Pro Glu Arg Phe Ile Glu Lys Phe Ala Ala
65                  70                  75                  80

Tyr Gly Cys Glu Ile Ile Tyr Val His Leu Glu Thr Cys Lys His Ile
                85                  90                  95

Ser Arg Thr Leu Leu Lys Ile Lys Glu Ser Lys Val Lys Ser Gly Val
                100                 105                 110

Ala Leu Asn Pro Gly Thr Pro Ile Asn Leu Ile Glu Glu Val Leu Gly
            115                 120                 125

Asp Val Asp Tyr Val Leu Ile Met Ala Val Asn Pro Gly Phe Ala Gly
130                 135                 140

Gln Asn Phe Ile Glu Ser Thr Val Asp Lys Val Ala Arg Leu Lys Lys
145                 150                 155                 160

Met Ile Asp Lys Lys Gly Tyr His Ile Lys Ile Ala Ile Asp Gly Gly
                165                 170                 175

Ile Asn Glu Met Asn Ile Pro Lys Leu Tyr Ser Ala Gly Ala Glu Tyr
            180                 185                 190

Phe Val Val Gly Thr Ala Gly Leu Phe Asn Lys Asn Gly Lys Tyr Lys
        195                 200                 205

Glu Asn Ile Ser Lys Leu Lys Asn Ser Ile Phe Lys
210                 215                 220

<210> SEQ ID NO 14
<211> LENGTH: 225
<212> TYPE: PRT
<213> ORGANISM: Thermoanaerobacterium thermosaccharolyticum

<400> SEQUENCE: 14

Met Lys Pro Met Phe Ala Pro Ser Leu Met Cys Ala Asn Phe Leu Asp
1               5                   10                  15

Leu Lys Asn Gln Ile Glu Ile Leu Asn Glu Arg Ala Asp Ile Tyr His
                20                  25                  30

Ile Asp Ile Met Asp Gly His Tyr Val Lys Asn Phe Ala Leu Ser Pro
            35                  40                  45

Tyr Leu Met Glu Gln Leu Lys Thr Ile Ala Lys Ile Pro Met Asp Ala
    50                  55                  60

His Leu Met Val Glu Asn Pro Ala Asp Phe Leu Glu Cys Ile Ala Lys
65                  70                  75                  80

Ser Gly Ala Thr Tyr Ile Ser Pro His Ala Glu Thr Ile Asn Lys Asp
                85                  90                  95

Ala Phe Arg Ile Met Arg Thr Ile Lys Ala Leu Gly Cys Lys Thr Gly
                100                 105                 110

Ile Val Leu Asn Pro Ala Thr Pro Val Glu Tyr Ile Lys Tyr Tyr Ile
            115                 120                 125

Gly Met Leu Asp Lys Ile Thr Ile Leu Thr Val Asp Ala Gly Phe Ala
130                 135                 140

Gly Gln Thr Phe Ile Asn Glu Met Leu Asp Lys Ile Ala Glu Ile Lys
145                 150                 155                 160

Ser Leu Arg Asp Gln Asn Gly Tyr Ser Tyr Leu Ile Glu Val Asp Gly
                165                 170                 175

Ser Cys Asn Glu Lys Thr Phe Lys Gln Leu Ala Glu Ala Gly Thr Asp
                180                 185                 190

Val Phe Val Gly Ser Ser Gly Leu Phe Asn Leu Asp Thr Asp Leu
                195                 200                 205

Lys Val Ala Trp Asp Lys Met Met Asp Thr Phe Thr Arg Cys Thr Ser
210                 215                 220

Asn
225

<210> SEQ ID NO 15
<211> LENGTH: 234
<212> TYPE: PRT
<213> ORGANISM: Unknown
<220> FEATURE:
<223> OTHER INFORMATION: Thermoflavimicrobium dichotomicum

<400> SEQUENCE: 15

Met Gln Tyr Arg Arg Ile Thr Ile Ala Pro Ser Ile Met Cys Ala Asp
1               5                   10                  15

Leu Cys Asn Leu Glu Lys Ser Val Lys Glu Leu Glu Lys Glu Gly Phe
                20                  25                  30

Asp Thr Leu His Val Asp Ile Ile Asp Gly Tyr Phe Ser Pro Ser Met
            35                  40                  45

Pro Leu Gly Ile Asp Thr Ile Lys Gln Leu Arg Lys Ile Thr Asn Met
        50                  55                  60

Asn Phe Asp Ile His Ile Met Ala Asn Asn Glu Phe Phe Ile Gln
65                  70                  75                  80

Glu Met Ile Lys Ile Gly Val Gln Gln Ile Ser Phe His Val Glu Thr
                85                  90                  95

Ser Ile His Ile Asp Arg Tyr Ile Gln Leu Ile Lys Lys Asn Gly Ile
                100                 105                 110

Lys Val Gly Ile Ala Leu Asn Pro Ala Thr Ser Leu Ser Val Leu Asp
            115                 120                 125

Tyr Val Leu Pro Gln Cys Asp Thr Ile Leu Leu Met Leu Ile Asn Pro
        130                 135                 140

Gly Phe Ala Thr Asp Lys Asn Glu Lys Gln Val Ser Tyr Ala Ile Lys
145                 150                 155                 160

Lys Val Glu Asp Leu Tyr Gln Leu Ile Lys Glu Lys Gly Leu Asp Thr
                165                 170                 175

Arg Ile Glu Val Asp Gly Arg Val Ser Phe Asp Thr Ile Pro Gly Leu
            180                 185                 190

Val Arg Ala Gly Ala Asp Ile Leu Val Ala Gly Ser Thr Ser Leu Phe
        195                 200                 205

Met Pro Ser Asn Ser Leu Ala Glu Asn Lys Lys Ser Met Glu Lys Tyr
210                 215                 220

Ile Leu Glu Gly Leu Ser Glu Glu Val Lys
225                 230

<210> SEQ ID NO 16
<211> LENGTH: 222
<212> TYPE: PRT
<213> ORGANISM: Artificial Sequence

```
<220> FEATURE:
<223> OTHER INFORMATION: ribulose-phosphate 3-epimerase

<400> SEQUENCE: 16

Met Ser Val Leu Leu Cys Pro Ser Met Met Cys Ala His Phe Gly Asn
1               5                   10                  15

Leu Ala His Glu Val Ala Glu Leu Glu Ala Ala Gly Ile Asp Met Phe
            20                  25                  30

His Leu Asp Val Met Asp Gly Arg Phe Val Pro Asn Phe Gly Met Gly
        35                  40                  45

Leu Gln Asp Ile Glu Phe Ile Ala Ala His Ala Thr Lys Pro Ala Asp
    50                  55                  60

Val His Leu Met Ile Glu Asp Pro Gly Asn Tyr Val Glu Lys Phe Ala
65                  70                  75                  80

Lys Leu Gly Ile Lys Val Ile Tyr Thr His Pro Glu Ala Asp Tyr His
                85                  90                  95

Pro Ala Arg Thr Leu Leu Lys Ile Ala Asp Ala Gly Ala Ala Pro Gly
            100                 105                 110

Ile Ala Ile Asn Pro Gly Thr Pro Val Glu Ala Ile Glu Pro Leu Leu
        115                 120                 125

His Leu Ala Gln Tyr Val Leu Val Met Thr Val Asn Pro Gly Phe Ala
    130                 135                 140

Gly Gln Pro Tyr Leu Ser Phe Val Asp Glu Lys Val Asp Arg Leu Ala
145                 150                 155                 160

Glu Leu Lys Glu Arg Tyr Gly Tyr Arg Ile Val Ile Asp Gly Ala Cys
                165                 170                 175

Thr Ala Ala Val Val Glu Arg Leu Ala Pro Arg Gly Val Asp Gly Phe
            180                 185                 190

Val Leu Gly Thr Lys Gly Leu Phe Gly Arg Gly Lys Pro Tyr Gly Glu
        195                 200                 205

Val Ile Ala Glu Leu Arg Ser Arg Ser Gly Asp Cys Arg Arg
    210                 215                 220

<210> SEQ ID NO 17
<211> LENGTH: 228
<212> TYPE: PRT
<213> ORGANISM: Unknown
<220> FEATURE:
<223> OTHER INFORMATION: Aeribacillus pallidus

<400> SEQUENCE: 17

Met Thr Met Ile Gly Pro Ser Leu Met Cys Ala Asp Met Gly Asn Leu
1               5                   10                  15

Lys Met Asp Val Gln Glu Leu Asp Gln Ala Gly Val Asp Phe Phe His
            20                  25                  30

Ile Asp Ile Met Asp Gly Ser Phe Val Pro Asn Phe Thr Met Gly Pro
        35                  40                  45

Asp Met Val Asn Val Ile Arg Ala Ala Thr Asp Lys Pro Leu Asp Ile
    50                  55                  60

His Leu Met Ile Met Arg Pro Glu Glu His Ile Asn Leu Phe Ala Asp
65                  70                  75                  80

Ala Gly Ala Asp Met Ile Ser Val His Ile Glu Ser Thr Ile His Leu
                85                  90                  95

Gln Arg Val Leu Gln Thr Ile Lys Ser Lys Gly Ile Lys Ala Gly Val
            100                 105                 110
```

```
Ala Leu Asn Pro Ser Thr Pro Ile Glu Ser Ile Glu Tyr Val Met Asp
            115                 120                 125

Val Ile Asp Tyr Val Thr Leu Met Thr Val Asn Pro Gly Phe Ala Gly
130                 135                 140

Gln Lys Phe Ile Pro Thr Met Tyr Asn Lys Ile Lys Lys Leu His Gln
145                 150                 155                 160

Leu Ile Glu Lys Glu Ser Tyr Asn Ile Leu Ile Gln Val Asp Gly Asn
            165                 170                 175

Ile Gly Tyr Glu Thr Ile Pro Lys Val Leu Glu Asn Gly Ala Lys Met
            180                 185                 190

Leu Val Cys Gly Thr Ser Ser Leu Phe Lys Ser Lys Gly Ser Leu His
            195                 200                 205

Asp Ala Val Ile His Leu Arg Gln Phe Ile Glu Gly Thr Ala Lys Val
210                 215                 220

Lys Thr Gly Asp
225
```

<210> SEQ ID NO 18
<211> LENGTH: 232
<212> TYPE: PRT
<213> ORGANISM: Unknown
<220> FEATURE:
<223> OTHER INFORMATION: Geobacillus thermocatenulatus

<400> SEQUENCE: 18

```
Met Ile Leu Ile Gly Pro Ser Leu Met Cys Ala Asp Met Gly Asn Leu
1               5                   10                  15

Arg Asp Asn Val Ile Arg Leu Asp Lys Ala Gly Val Asp Tyr Phe His
            20                  25                  30

Phe Asp Ile Met Asp Gly Lys Phe Val Pro Asn Phe Thr Met Gly Pro
            35                  40                  45

Asp Ile Ile Arg Ala Leu Arg Asn Phe Thr Asn Lys Pro Phe Asp Val
50                  55                  60

His Leu Met Ile Glu Lys Pro Glu His Leu Gly Leu Phe Ile Asp
65                  70                  75                  80

Ala Gly Ala Asp Met Ile Ser Val His Val Glu Ala Thr Leu His Leu
            85                  90                  95

Gln Arg Thr Leu Gln Lys Ile Arg Asp Ser Gly Leu Lys Ala Gly Val
            100                 105                 110

Ala Leu Asn Pro Ser Thr Pro Ile Ser Thr Ile Glu Tyr Val Leu Asp
            115                 120                 125

Thr Val Asp Tyr Ile Thr Val Met Thr Val Asn Pro Gly Phe Ala Gly
130                 135                 140

Gln Lys Phe Ile Pro Leu Met Lys Lys Lys Ile Ser Lys Leu Lys Glu
145                 150                 155                 160

Leu Ile Thr Glu Ala Asp Tyr Asp Val Asn Ile Gln Val Asp Gly Asn
            165                 170                 175

Ile Gly Tyr Gln Thr Met Thr Ala Val Leu Glu Asn Gly Ala Asn Met
            180                 185                 190

Leu Val Leu Gly Thr Ser Cys Leu Phe Lys Lys Glu Leu Ala Leu Glu
            195                 200                 205

Asp Ala Val Leu Arg Leu Arg Gln Phe Ile Asp Ser Phe Gln Ile Gln
210                 215                 220

Ser Ser Leu Arg Ser Lys Glu Lys
225                 230
```

<210> SEQ ID NO 19
<211> LENGTH: 224
<212> TYPE: PRT
<213> ORGANISM: Unknown
<220> FEATURE:
<223> OTHER INFORMATION: Mahella australiensis 50-1 BON

<400> SEQUENCE: 19

Met Lys Ala Lys Ile Ser Pro Ser Met Met Cys Ala Asp Phe Gly Arg
1               5                   10                  15

Leu Glu Asp Glu Ile Arg Ile Leu Gly Lys Ala Gly Val Asp Tyr Leu
            20                  25                  30

His Ile Asp Val Met Asp Gly His Phe Val Pro Asn Phe Ala Ile Gly
        35                  40                  45

Pro Asp Leu Thr Arg Ser Ile Arg Arg Leu Thr Asp Ile Pro Leu Asp
    50                  55                  60

Ile His Leu Met Val Glu Arg Pro Glu Asn Tyr Ile Asp Leu Phe Glu
65                  70                  75                  80

Pro Arg Leu Gly Asp Ile Val Ser Val His Gln Ala Thr Val His
                85                  90                  95

Leu Glu Arg Thr Leu Gln Ile Ile Lys Ala Ala Gly Ala Lys Thr Gly
            100                 105                 110

Val Ala Val Asn Pro Ala Thr Pro Ala Ile Met Ile Lys Pro Val Ile
        115                 120                 125

Asp Glu Ala Asp Val Val Leu Val Met Thr Val Asn Pro Gly Phe Ala
    130                 135                 140

Gly Gln Lys Leu Val Pro Ser Thr Leu Ser Lys Ile Arg Glu Val Lys
145                 150                 155                 160

Glu Met Ile Gln Glu Ser Cys Ala Ser Ala Glu Ile Glu Val Asp Gly
                165                 170                 175

Asn Val Ser Phe Glu Asn Ala Phe Lys Met Leu Ala Ala Gly Ala Asp
            180                 185                 190

Ile Phe Val Ala Gly Thr Ser Ser Ile Phe Asn Ala Asp Met Asp Lys
        195                 200                 205

Leu Glu Ala Ala Tyr Lys Leu Lys Gln Ile Leu Ser Val Lys Glu Gly
    210                 215                 220

<210> SEQ ID NO 20
<211> LENGTH: 222
<212> TYPE: PRT
<213> ORGANISM: Unknown
<220> FEATURE:
<223> OTHER INFORMATION: Thermoanaerobacterium sp. PSU-2

<400> SEQUENCE: 20

Met Lys Glu Ile Lys Ile Val Pro Ser Leu Met Cys Cys Asp Phe Leu
1               5                   10                  15

Asn Leu Asn Asn Glu Ile Lys Asp Leu Glu Lys Ser Gly Val Asp Leu
            20                  25                  30

Phe His Ile Asp Ile Met Asp Gly Asn Phe Val Asp Asn Phe Ala Met
        35                  40                  45

Ser Gly Thr Glu Ile Lys Ser Ile Lys Arg Ile Thr Asn Ile Pro Leu
    50                  55                  60

Asp Val His Leu Met Val Lys Glu Pro Leu Arg Tyr Ile Lys Tyr Phe
65                  70                  75                  80

Val Asp Ala Gly Ala Asp Ile Ile Thr Val His Ile Glu Ala Cys Thr
            85                  90                  95

His Leu Asn Arg Thr Leu Gln Glu Ile Lys Asn Asn Val Lys Val
            100                 105                 110

Gly Ile Ala Leu Asn Pro Gly Thr Ser His Leu Leu Glu Pro Ile
            115                 120                 125

Val Asp Tyr Leu Asp Ile Val Leu Ile Met Ala Val Asn Pro Gly Phe
130                 135                 140

Ala Gly Gln Asp Phe Ile Pro Ser Thr Val Asn Lys Val Lys Lys Thr
145                 150                 155                 160

Arg Asp Phe Leu Asn Ser Leu Gly Phe Asn Asn Val Glu Ile Glu Val
            165                 170                 175

Asp Gly His Ile Asp Ile Gln Thr Ile Pro Pro Leu Tyr Asp Ala Gly
            180                 185                 190

Ala Arg Ile Phe Val Ala Gly Thr Ala Gly Leu Phe Tyr Gly Asp Arg
            195                 200                 205

Asn Tyr Glu Glu Asn Val Lys Lys Leu Arg Ser Cys Val Tyr
210                 215                 220

<210> SEQ ID NO 21
<211> LENGTH: 218
<212> TYPE: PRT
<213> ORGANISM: Thermoanaerobacterium thermosaccharolyticum

<400> SEQUENCE: 21

Met Ile Lys Ile Cys Pro Ser Leu Met Cys Ala Asp Phe Thr Lys Leu
1               5                   10                  15

Lys Asp Glu Ile Leu Glu Leu Glu Arg Ala Gly Ala Asp Met Phe His
            20                  25                  30

Leu Asp Ile Met Asp Gly Asn Phe Val Pro Asn Phe Ala Leu Gly Ile
            35                  40                  45

Glu Asp Val Lys Ala Val Ser Lys Ile Ala Ser Ile Pro Tyr Asp Ile
50                  55                  60

His Leu Met Ile Glu Glu Pro Glu Arg Tyr Val Glu Lys Phe Ser Lys
65                  70                  75                  80

Tyr Gly Cys Lys Ile Met Tyr Val His Leu Glu Thr Cys Lys His Ile
            85                  90                  95

Ser Arg Thr Leu Leu Lys Ile Lys Glu Arg Asn Val Lys Ala Gly Leu
            100                 105                 110

Ala Leu Asn Pro Gly Thr Pro Ile Ser Phe Ala Glu Glu Val Leu Ser
            115                 120                 125

Asp Val Glu Tyr Ile Leu Ile Met Ala Val Asn Pro Gly Phe Ala Gly
130                 135                 140

Gln Ser Phe Ile Glu Ser Thr Val Asp Lys Val Ser Arg Leu Lys Asp
145                 150                 155                 160

Leu Ile Asp Lys Lys Gly Tyr Asp Ile Lys Ile Ala Val Asp Gly Cys
            165                 170                 175

Ile Asn Glu Val Thr Val Lys Lys Leu Tyr Asn Val Gly Ala Glu Tyr
            180                 185                 190

Phe Ile Ala Gly Thr Ala Gly Leu Phe Asn Lys Asn Gly Ser Tyr Ser
            195                 200                 205

Glu Asn Ile Asn Arg Leu Lys Asn Ile Leu
210                 215

-continued

```
<210> SEQ ID NO 22
<211> LENGTH: 221
<212> TYPE: PRT
<213> ORGANISM: Unknown
<220> FEATURE:
<223> OTHER INFORMATION: Tepidanaerobacter syntrophicus

<400> SEQUENCE: 22
```

Met Thr Ile Glu Ile Ser Ser Leu Met Cys Ala Asp Leu Leu Asn
1               5                   10                  15

Leu Glu Ser Glu Ile Leu Lys Leu Glu Lys Ala Gly Thr Asp Met Phe
            20                  25                  30

His Met Asp Ile Met Asp Gly His Phe Val Asn Asn Leu Ala Leu Ser
        35                  40                  45

Ile Asp Leu Leu Lys Ala Ile Arg Ser Val Ser Thr Thr Pro Leu Glu
    50                  55                  60

Ala His Leu Met Val Glu Asn Pro Leu Asn Tyr Ile Glu Lys Ala Lys
65                  70                  75                  80

Lys Ala Gly Ala Asp Ile Ile Ser Val His Leu Glu Ser Thr Pro His
                85                  90                  95

Ile His Lys Ala Leu Lys Glu Ile Arg Glu Cys Asn Met Lys Ala Gly
            100                 105                 110

Ile Ala Ile Asn Pro Gly Thr Ser His Leu Leu Ile Glu Pro Leu Leu
        115                 120                 125

Glu Glu Thr Asp Phe Ile Leu Thr Met Ala Val Asn Pro Gly Phe Ala
    130                 135                 140

Gly Gln Glu Phe Ile Lys Ser Thr Val Asn Lys Val Tyr Lys Ile Asn
145                 150                 155                 160

Glu Met Leu Lys Glu Asn His Leu Thr Asn Ile Lys Ile Glu Val Asp
                165                 170                 175

Gly Asn Ile Asn Ser Glu Thr Ile Pro Pro Leu Tyr Asn Ala Gly Ala
            180                 185                 190

Arg Ile Phe Val Gly Gly Thr Ser Gly Ile Phe Phe Gly Asp Arg Asn
        195                 200                 205

Tyr Glu Arg Asn Ile Glu Asn Leu Lys Asn Ser Ile Lys
    210                 215                 220

```
<210> SEQ ID NO 23
<211> LENGTH: 238
<212> TYPE: PRT
<213> ORGANISM: Unknown
<220> FEATURE:
<223> OTHER INFORMATION: Ardenticatenia bacterium

<400> SEQUENCE: 23
```

Met Ala Arg Ala Phe Pro Ile Gln Ile Ala Pro Ser Met Met Cys Ala
1               5                   10                  15

Asp Ile Trp Gln Leu Ala Glu Gln Val His Gln Leu Glu Gln Ala Gly
            20                  25                  30

Val Asp Tyr Leu His Phe Asp Ile Met Asp Ala His Phe Val Pro Asn
        35                  40                  45

Met Pro Val Gly Leu Val Phe Leu Glu Gln Leu Arg Pro His Thr Gln
    50                  55                  60

Leu Pro Phe Asp Val His Leu Met Val Asp Asn Asn Asp Phe Phe Val
65                  70                  75                  80

Pro Leu Leu Val Ala Ile Gly Val Gln Ser Ile Ser Val His Val Glu
                85                  90                  95

-continued

```
Ser Ala Val His Leu Asp Arg Thr Leu Thr Leu Ile Arg Ser His Gly
            100                 105                 110

Ile Lys Ala Gly Val Ala Leu Asn Pro Ala Thr Pro Leu Ser Val Leu
            115                 120                 125

Arg Tyr Val Thr Glu Gln Met Asp Tyr Val Leu Ile Met Thr Val Asn
        130                 135                 140

Pro Gly Phe Ala Gly Gln Arg Met Val Pro Ser Ala Tyr Arg Lys Ile
145                 150                 155                 160

Arg Asp Cys Cys Leu Phe Leu Gln Glu Asn Gly Val Asp Ile Pro Ile
                165                 170                 175

Gln Val Asp Gly Asn Val Ser Phe Asp Arg Ile Pro His Met Val Ala
            180                 185                 190

Ala Gly Ala Asp Ile Leu Val Thr Gly Thr Ser Ser Val Phe His Arg
        195                 200                 205

Asp Gly Thr Leu Leu Glu Asn Ile Ala Arg Thr Arg Gln Ala Ile Ala
210                 215                 220

Glu Gly Leu Arg Met Arg Arg His Asp Asn Leu Arg Ile Thr
225                 230                 235
```

<210> SEQ ID NO 24
<211> LENGTH: 254
<212> TYPE: PRT
<213> ORGANISM: Unknown
<220> FEATURE:
<223> OTHER INFORMATION: Firmicutes bacterium HGW-Firmicutes-5

<400> SEQUENCE: 24

```
Met Glu Val Ile Lys Met Ser Lys Phe Asn Lys Lys Ile Ser Pro Ser
1               5                   10                  15

Ile Met Cys Gly Asp Trp Leu Asn Ile Glu Lys Met Ile Tyr Gln Leu
            20                  25                  30

Glu Ala Ala Lys Ala Asp Trp Ile His Val Asp Ile Met Asp Gly His
        35                  40                  45

Tyr Val Pro Asn Ile Thr Phe Gly Ile Asp Met Val Asn Gln Ile Arg
    50                  55                  60

Arg Ile Val Asp Ile Pro Leu Asp Val His Met Met Ala Tyr His Pro
65                  70                  75                  80

Glu Lys Phe Phe Glu Arg Phe Glu Leu Asp Gln Arg Asp Ile Ile Thr
                85                  90                  95

Val His Tyr Glu Glu Ile Glu Asn Leu Asp Lys Val Ile Met Leu Leu
            100                 105                 110

Lys Gln Lys Lys Ile Lys Val Gly Ile Ala Leu Lys Pro Glu Thr Asp
        115                 120                 125

Ile Ser Val Leu Ser Pro Tyr Leu Asp Asp Ile Asn Ile Val Leu Leu
    130                 135                 140

Met Met Asn Lys Pro Gly Gly Tyr Gly Arg Ala Met Glu Val Gly Met
145                 150                 155                 160

Met Asp Lys Ile Arg Asp Thr Lys Ala Leu Ile Thr Gly Ser Gly Lys
                165                 170                 175

Lys Val Leu Ile Glu Val Asp Gly Ser Val Ser Tyr Ala Leu Ala Gly
            180                 185                 190

Asp Met Ser Tyr Ala Gly Ala Asp Val Phe Val Ala Gly Thr Ser Ser
        195                 200                 205

Ile Phe Asn Lys Glu Met Asp Leu Arg Ser Gly Val Gln Lys Leu Arg
    210                 215                 220
```

Gly Ile Val Asn His Ile Arg Thr Asp Gln Asn Ile Gln Lys Leu Ala
225                 230                 235                 240

Ser Val Asn Asp Lys Lys Glu Leu Ile Lys Tyr Ser Val Ser
                245                 250

<210> SEQ ID NO 25
<211> LENGTH: 231
<212> TYPE: PRT
<213> ORGANISM: Unknown
<220> FEATURE:
<223> OTHER INFORMATION: Aeribacillus pallidus

<400> SEQUENCE: 25

Met Gln Asn Asn Lys Lys Ile Thr Ile Ala Pro Ser Ile Met Cys Ala
1               5                   10                  15

Asp Leu Cys Asn Leu Glu Lys Ser Val Lys Glu Ile Glu Lys Glu Gly
                20                  25                  30

Leu Asp Thr Leu His Ile Asp Ile Asp Gly His Phe Ser Pro Ser
            35                  40                  45

Met Pro Leu Gly Ile Asp Thr Ile Lys Gln Leu Arg Lys Ile Thr Asp
    50                  55                  60

Met Asn Phe Asp Val His Ile Met Ser Asn Asn Glu Phe Ile
65                  70                  75                  80

Gln Glu Met Ile Lys Ile Asp Val Gln Gln Ile Ser Phe His Tyr Glu
                85                  90                  95

Thr Ser Thr His Ile Asp Arg Tyr Ile Asn Leu Ile Lys Asn Asn Gly
            100                 105                 110

Ile Lys Ala Gly Leu Ala Leu Asn Pro Ala Thr Pro Leu Ser Val Leu
    115                 120                 125

Asp Tyr Ile Leu Pro Lys Cys Asp Thr Ile Leu Leu Met Leu Ile Asn
130                 135                 140

Pro Gly Phe Ala Thr Asp Glu Asn Glu Lys Gln Val Ser Tyr Ala Ile
145                 150                 155                 160

Lys Lys Val Glu Asp Leu Ala Arg Leu Ile Lys Glu Lys Glu Leu Asp
                165                 170                 175

Thr Asn Ile Glu Val Asp Gly Arg Val Ser Leu Asp Thr Ile Pro Ser
            180                 185                 190

Leu Val Lys Ala Gly Ala Asp Ile Leu Val Ala Gly Ser Thr Ser Leu
    195                 200                 205

Phe Ile Arg Asp Lys Ser Leu Ala Glu Asn Lys Lys Ala Met Glu Lys
210                 215                 220

Cys Ile Ile Glu Gly Leu Leu
225                 230

<210> SEQ ID NO 26
<211> LENGTH: 226
<212> TYPE: PRT
<213> ORGANISM: Unknown
<220> FEATURE:
<223> OTHER INFORMATION: Epulopiscium sp. SCG-B05WGA-EpuloA1

<400> SEQUENCE: 26

Met Lys Lys Tyr Ile Ser Thr Ser Leu Met Cys Leu Asp Leu Met Glu
1               5                   10                  15

Ala Lys Asn Gly Ile Ile Ala Leu Glu Gln Val Gly Met Asp Tyr Phe
                20                  25                  30

His Met Asp Val Met Asp Asn His Phe Val Pro Asn Phe Ser Leu Ser
            35                  40                  45

Ser Asp Phe Ile Lys Val Thr Arg Lys Cys Thr Gln Val Pro Leu Asp
            50                  55                  60

Ile His Leu Met Ile Glu Asn Pro Glu Asn Ser Leu His Leu Phe Asp
65                  70                  75                  80

Gly Ala Asn Glu Gly Asp Ile Leu Ser Ile His Tyr Glu Ser Thr Lys
                85                  90                  95

His Val Gln Lys Val Leu Ser Glu Ile Arg Lys Met Gly Tyr Lys Ala
            100                 105                 110

Gly Ile Ala Leu Asn Pro Ala Thr Pro Leu Asn Val Leu Glu Glu Val
            115                 120                 125

Ile Glu Asp Leu Asp Met Val Leu Ile Met Thr Val Asn Pro Gly Phe
130                 135                 140

Ala Gly Gln Lys Leu Ile Pro Ser Thr Leu Gly Lys Ile Gln Lys Cys
145                 150                 155                 160

Lys Asp Phe Leu Val Lys Val Gly Ala Glu Asn Ile Leu Ile Glu Val
                165                 170                 175

Asp Gly Asn Val Ser Phe Glu Asn Ala Val Lys Met Asn Lys Met Gly
            180                 185                 190

Ala Asp Ile Phe Val Ala Gly Thr Ser Ser Val Phe Ser Lys Glu Gly
            195                 200                 205

Thr Leu Glu Glu Asn Thr Lys Lys Met Arg Lys Ile Leu Glu Gly Ser
210                 215                 220

Leu Cys
225

<210> SEQ ID NO 27
<211> LENGTH: 4
<212> TYPE: PRT
<213> ORGANISM: Artificial Sequence
<220> FEATURE:
<223> OTHER INFORMATION: Motif

<400> SEQUENCE: 27

Ser Ile Met Cys
1

<210> SEQ ID NO 28
<211> LENGTH: 4
<212> TYPE: PRT
<213> ORGANISM: Artificial Sequence
<220> FEATURE:
<223> OTHER INFORMATION: Motif

<400> SEQUENCE: 28

Ser Met Met Cys
1

<210> SEQ ID NO 29
<211> LENGTH: 4
<212> TYPE: PRT
<213> ORGANISM: Artificial Sequence
<220> FEATURE:
<223> OTHER INFORMATION: Motif

<400> SEQUENCE: 29

Ser Leu Met Cys
1

<210> SEQ ID NO 30
<211> LENGTH: 4

```
<212> TYPE: PRT
<213> ORGANISM: Artificial Sequence
<220> FEATURE:
<223> OTHER INFORMATION: Motif

<400> SEQUENCE: 30

Ser Val Met Cys
1

<210> SEQ ID NO 31
<211> LENGTH: 6
<212> TYPE: PRT
<213> ORGANISM: Artificial Sequence
<220> FEATURE:
<223> OTHER INFORMATION: Motif

<400> SEQUENCE: 31

Gly Asn Ser Gly Leu Phe
1               5

<210> SEQ ID NO 32
<211> LENGTH: 12
<212> TYPE: PRT
<213> ORGANISM: Artificial Sequence
<220> FEATURE:
<223> OTHER INFORMATION: Motif

<400> SEQUENCE: 32

Gly Ser Ser Gly Leu Phe Gly Ser Ser Ser Leu Phe
1               5                   10

<210> SEQ ID NO 33
<211> LENGTH: 6
<212> TYPE: PRT
<213> ORGANISM: Artificial Sequence
<220> FEATURE:
<223> OTHER INFORMATION: Motif

<400> SEQUENCE: 33

Gly Ser Thr Ser Leu Phe
1               5

<210> SEQ ID NO 34
<211> LENGTH: 6
<212> TYPE: PRT
<213> ORGANISM: Artificial Sequence
<220> FEATURE:
<223> OTHER INFORMATION: Motif

<400> SEQUENCE: 34

Gly Thr Ala Gly Leu Phe
1               5

<210> SEQ ID NO 35
<211> LENGTH: 6
<212> TYPE: PRT
<213> ORGANISM: Artificial Sequence
<220> FEATURE:
<223> OTHER INFORMATION: Motif

<400> SEQUENCE: 35

Gly Thr Lys Gly Leu Phe
1               5

<210> SEQ ID NO 36
<211> LENGTH: 6
<212> TYPE: PRT
```

```
<213> ORGANISM: Artificial Sequence
<220> FEATURE:
<223> OTHER INFORMATION: Motif

<400> SEQUENCE: 36

Gly Thr Gln Ser Leu Phe
1               5

<210> SEQ ID NO 37
<211> LENGTH: 6
<212> TYPE: PRT
<213> ORGANISM: Artificial Sequence
<220> FEATURE:
<223> OTHER INFORMATION: Motif

<400> SEQUENCE: 37

Gly Thr Ser Cys Leu Phe
1               5

<210> SEQ ID NO 38
<211> LENGTH: 6
<212> TYPE: PRT
<213> ORGANISM: Artificial Sequence
<220> FEATURE:
<223> OTHER INFORMATION: Motif

<400> SEQUENCE: 38

Gly Thr Ser Gly Leu Phe
1               5

<210> SEQ ID NO 39
<211> LENGTH: 6
<212> TYPE: PRT
<213> ORGANISM: Artificial Sequence
<220> FEATURE:
<223> OTHER INFORMATION: Motif

<400> SEQUENCE: 39

Gly Thr Ser Ser Ile Phe
1               5

<210> SEQ ID NO 40
<211> LENGTH: 6
<212> TYPE: PRT
<213> ORGANISM: Artificial Sequence
<220> FEATURE:
<223> OTHER INFORMATION: Motif

<400> SEQUENCE: 40

Gly Thr Ser Gly Ile Phe
1               5

<210> SEQ ID NO 41
<211> LENGTH: 6
<212> TYPE: PRT
<213> ORGANISM: Artificial Sequence
<220> FEATURE:
<223> OTHER INFORMATION: Motif

<400> SEQUENCE: 41

Gly Thr Ser Ser Leu Phe
1               5

<210> SEQ ID NO 42
<211> LENGTH: 6
<212> TYPE: PRT
<213> ORGANISM: Artificial Sequence
```

```
<220> FEATURE:
<223> OTHER INFORMATION: Motif

<400> SEQUENCE: 42

Gly Thr Ser Ser Val Phe
1               5
```

RIBULOSE-PHOSPHATE 3-EPIMERASE MOTIF HAVING LOW SIDE REACTIVITY AND ENZYME INCLUDING THE SAME

SEQUENCE LISTING SUBMISSION VIA EFS-WEB

A computer readable text file, entitled "SequenceListing.txt" created on Oct. 11, 2022 with a file size of 47,142 bytes contains the sequence listing for this application and is hereby incorporated by reference in its entirety.

BACKGROUND OF THE INVENTION

1. Field of the Invention

The present disclosure relates to ribulose-phosphate 3-epimerase, in particular, ribulose-phosphate 3-epimerase having low psicose 3-epimerization activity, a composition for producing psicose-6-phosphate or psicose, the composition including the same, and a method of producing psicose-6-phosphate or psicose using the same.

2. Description of the Related Art

Psicose (allulose), which is an epimer of fructose at position C3, is a monosaccharide known as a rare sugar found in extremely small quantities in nature. Psicose has approximately 70% the sweetness of sucrose with almost zero calories, and has received much attention as a new food raw material used in functional foods due to functions such as inhibition of blood glucose increase, fat synthesis, etc.

Due to these characteristics, psicose is being considered for use in various foods as a sugar substitute sweetener. However, since it exists in very small amounts in nature, there is a continuous demand for a method capable of efficiently producing psicose.

One of the known methods of producing psicose is a process of producing psicose-6-phosphate through conversion to glucose or glucose-1-phosphate, glucose-6-phosphate, and fructose-6-phosphate (Korean Patent Publication No. 10-2018-0004023), but there is an increasing demand for the development of a technology for more efficient and economical psicose production.

Psicose 3-epimerase (D-psicose 3-epimerase, EC 5.1.3.30) is known as an enzyme capable of producing allulose by 3-epimerization (C3 epimerization) of fructose (D-fructose). When allulose is produced from fructose by way of a single enzymatic reaction using the above enzyme, there is a certain level of reaction equilibrium between the substrate fructose and the product allulose (product/substrate=about 20% to 35%). Therefore, in the case of producing high-purity allulose using the single enzymatic reaction, an additional purification process of separating and removing a high concentration of fructose from the reaction resultant is required.

In addition, since the previously known psicose-6-phosphate 3-epimerases have psicose 3-epimerization activity, they cannot be called psicose-6-phosphate 3-epimerization-specific enzymes and are not suitable for practical psicose production (WO 2018/129275. WO 2018/112139).

Through investigation of specific motif sequences that may influence psicose 3-epimerization activity, the present inventors found that specific motifs are specifically critical for psicose-6-phosphate 3-epimerization.

SUMMARY OF THE INVENTION

An object of the present disclosure is to provide ribulose-phosphate 3-epimerase.

Another object of the present disclosure is to provide a nucleic acid encoding the ribulose-phosphate 3-epimerase.

Still another object of the present disclosure is to provide a transformant including the nucleic acid encoding the ribulose-phosphate 3-epimerase.

Still another object of the present disclosure is to provide a composition for producing psicose-6-phosphate, the composition including the ribulose-phosphate 3-epimerase, a microorganism expressing the ribulose-phosphate 3-epimerase, or a culture of the microorganism.

Still another object of the present disclosure is to provide a method of producing psicose-6-phosphate, the method including the step of bringing fructose-6-phosphate into contact with the ribulose-phosphate 3-epimerase, the microorganism expressing the ribulose-phosphate 3-epimerase, or the culture of the microorganism.

Still another object of the present disclosure is to provide a composition for producing psicose, the composition including the ribulose-phosphate 3-epimerase, the microorganism expressing the ribulose-phosphate 3-epimerase, or the culture of the microorganism.

Still another object of the present disclosure is to provide a method of producing psicose, the method including the step of bringing fructose-6-phosphate into contact with the ribulose-phosphate 3-epimerase, the microorganism expressing the ribulose-phosphate 3-epimerase, or the culture of the microorganism.

BRIEF DESCRIPTION OF THE DRAWINGS

FIG. 1 shows a protein structure predicted from an amino acid sequence of ribulose-phosphate 3-epimerase (SEQ ID NO: 9: KPL22606); and FIG. 2 shows an HPLC histogram showing a previously known psicose-6-phosphate 3-epimerase (ADL69228; solid line) and an enzyme of the present disclosure (SEQ ID NO: 20; dotted line).

DETAILED DESCRIPTION OF THE PREFERRED EMBODIMENTS

Hereinafter, the present disclosure will be described in detail as follows. Meanwhile, each description and embodiment disclosed in this disclosure may also be applied to other descriptions and embodiments. That is, all combinations of various elements disclosed in this disclosure fall within the scope of the present disclosure. Further, the scope of the present disclosure is not limited by the specific description described below.

To achieve the above objects, an aspect of the present disclosure provides ribulose-phosphate 3-epimerase.

Specifically, the ribulose-phosphate 3-epimerase of the present disclosure may be a ribulose-phosphate 3-epimerase including a motif I consisting of an amino acid sequence of SEQ ID NO: 1 and a motif III consisting of an amino acid sequence of SEQ ID NO: 3 and having high activity and heat resistance, and more specifically not including a motif II consisting of an amino acid sequence of SEQ ID NO: 2, but is not limited thereto.

As used herein, the term "ribulose-phosphate 3-epimerase" refers to an enzyme, of which ribulose-phosphate 3-epimerase activity is known, or which has ribulose-phosphate 3-epimerase activity, and in particular, an enzyme which may act as a fructose-6-phosphate 3-epimerase or psicose-6-phosphate 3-epimerase. When the ribulose-phosphate 3-epimerase has the fructose-6-phosphate 3-epimerase activity or the psicose-6-phosphate 3-epimerase activity, it may include an amino acid sequence having deletion, modification, substitution, conservative substitution, or addition of some sequences.

Specifically, the enzyme of the present disclosure is an enzyme having reversible conversion activity of reversibly converting psicose-6-phosphate to fructose-6-phosphate or fructose-6-phosphate to psicose-6-phosphate, and in the present disclosure, the term "ribulose-phosphate 3-epimerase" may be used interchangeably with "psicose-6-phosphate 3-epimerase" or "enzyme".

The enzyme of the present disclosure may be an enzyme that converts glucose-1-phosphate (D-glucose-1-phosphate), glucose-6-phosphate (D-glucose-6-phosphate), or fructose-6-phosphate (D-fructose-6-phosphate) to psicose-8-phosphate, when these are mixed with each other. For example, the enzyme of the present disclosure may exhibit a conversion rate of 1% or more, 10% or more, or 30% or more into psicose-6-phosphate, when mixed with an equal amount of psicose-6-phosphate, glucose-1-phosphate, glucose-6-phosphate, and fructose-6-phosphate. As described, due to the selective activity of the enzyme of the present disclosure, it may exhibit a high psicose conversion rate in one-pot enzymatic conversion in which a plurality of enzymes and substrates are used at the same time.

As used herein, the "motif" refers to a part (region) having a specific sequence in an enzyme sequence, and may refer to a sequence having a specific protein function or activity, and may be a sequence conserved between microorganism species, but is not limited thereto. The ribulose-phosphate 3-epimerase of the present disclosure may include a motif I consisting of an amino acid sequence of SEQ ID NO: 1 and a motif III consisting of an amino acid sequence of SEQ ID NO: 3. Additionally, the ribulose-phosphate 3-epimerase may be characterized in that it does not include a motif II consisting of an amino acid sequence of SEQ ID NO: 2. Since the enzyme does not include the motif II, it may be characterized by having low psicose-3-epimerization activity, but is not limited thereto.

Specifically, the enzyme may have 5% or less, 4% or less, 3% or less, 2% or less, or 1% or less of activity of converting psicose to fructose, or no activity thereof, as compared with an enzyme without motif I and motif III, but is not limited thereto.

Further, the enzyme of the present disclosure may further include a motif consisting of an amino acid sequence of SEQ ID NO: 4 or 5.

The enzyme of the present disclosure is characterized by including or essentially including a specific motif, and also not including a specific motif. Specifically, the motifs I and III of the present disclosure may be included in a site (binding site) of the enzyme, which partially or wholly binds to a substrate and/or a metal ion (e.g., Mg, Mn, Zn, etc.) and reacts thereto, and may remain the own activity of the enzyme while reducing side reactivity. More specifically the motifs I and III may be included in a TIM-barrel fold in the binding site. An enzyme "including" a specific motif may further include or may not include another motif, domain, amino acid sequence, fragment, etc. in addition to the corresponding motif, and an enzyme "essentially including" a specific motif may essentially include the corresponding motif to obtain a desired property or characteristic, and may also include or may not include another motif, domain, amino acid sequence, fragment, etc. in addition to the corresponding motif, but is not limited thereto. An enzyme "not including" a specific motif may not include a sequence corresponding to the corresponding motif in the enzyme, and may include insertion, substitution, or deletion of another amino acid sequence at the location of the corresponding motif, or a combination thereof, but is not limited thereto.

Further, the motifs included or not included in the enzyme of the present disclosure may be included or may not be included each independently, and they are not limited to a specific arrangement order or position.

For example, the enzyme of the present disclosure may be an enzyme including only the motif I of SEQ ID NO: 1: an enzyme including the motif I of SEQ ID NO: 1 and the motif III of SEQ ID NO: 3 without the motif II of SEQ ID NO: 2; or an enzyme including the motif I of SEQ ID NO: 1, the motif III of SEQ ID NO: 3, and motifs of SEQ ID NOs: 4 and 5 without the motif II of SEQ ID NO: 2, but is not limited thereto.

As used herein, the "motif I" may consist of the amino acid sequence of the following SEQ ID NO: 1. It is apparent that a sequence including insertion, substitution, deletion, etc. of meaningless amino acid residues may also be included in the motif I of the present disclosure, as long as it does not influence the activity of the amino acid sequence of SEQ ID NO: 1.

```
Motif I (SEQ ID NO: 1):
V-D-G
```

The motif I may be included in a binding site that reacts with a substrate of the ribulose-phosphate 3-epimerase and a metal ion, but is not limited thereto. Specifically, the motif may be located at amino acid positions 173 to 184 from a first amino acid of the N-terminus of the ribulose-phosphate 3-epimerase, but is not limited thereto. In other words, valine (V), which is the first amino acid residue of the motif I, may be located between positions 173 to 182, and glycine (G), which is the last residue of the motif I, may be located between positions 175 to 184 from the first amino acid of the N-terminus of the ribulose-phosphate 3-epimerase, but is not limited thereto.

In a domain in which first beta-sheet structure-coil structure-alpha-helix structure-second beta-sheet structure are connected, the first amino acid residue of the motif I may start at the C-terminus toward the second beta-sheet, and the domain may be included in the binding site or may have a structure in which some regions overlap (FIG. 1).

As used herein, the "motif II" may consist of the amino acid sequence of the following SEQ ID NO: 2. It is apparent that a sequence including insertion, substitution, deletion, etc. of meaningless amino acid residues may also be included in the motif II of the present disclosure, as long as it does not influence the activity of the amino acid sequence of SEQ ID NO: 2.

```
Motif II (SEQ ID NO: 2):
M-X-X-D-P-G (X is any amino acid residue)
```

The motif II may be included in the N-terminal region of the ribulose-phosphate 3-epimerase, but is not limited thereto. Specifically, the motif may be located at amino acid positions 136 to 150 from the first amino acid of the N-terminus of the ribulose-phosphate 3-epimerase, but is not limited thereto. In other words, methionine (M), which is the first amino acid residue of the motif II, may be located between positions 136 to 145, and glycine (G), which is the last residue of the motif II, may be located between positions 141 to 150 from the first amino acid of the N-terminus of the ribulose-phosphate 3-epimerase, but is not limited thereto.

In the domain in which first beta-sheet structure-coil structure-alpha-helix structure-second beta-sheet structure are connected, the first amino acid residue of the motif II may start at the C-terminus of the first beta-sheet, and the domain may be included in the binding site or may have a structure in which some regions overlap, and the domain may be identical to the domain including the motif I (FIG. 1).

Specifically, X may include any amino acid without limitation, and specifically threonine (T) or valine (V), but is not limited thereto. More specifically the motif II may include a sequence of M-(T/A/M/L)-(V/N/I)-D-P-G, but is not limited thereto.

As used herein, the "motif III" may consist of the amino acid sequence of the following SEQ ID NO: 3. It is apparent that a sequence including insertion, substitution, deletion, etc. of meaningless amino acid residues may also be included in the motif III of the present disclosure, as long as it does not influence the activity of the amino acid sequence of SEQ ID NO: 3.

```
Motif III (SEQ ID NO: 3):
M-X-X-X'-P-G (X is any amino acid residue)
```

The motif III may be included in the N-terminal region of the ribulose-phosphate 3-epimerase, but is not limited thereto. Specifically, the motif may be located at amino acid positions 136 to 150 from the first amino acid of the N-terminus of the ribulose-phosphate 3-epimerase, but is not limited thereto. In other words, methionine (M), which is the first amino acid residue of the motif III, may be located between positions 136 to 145, and glycine (G), which is the last residue of the motif III, may be located between positions 141 to 150 from the first amino acid of the N-terminus of the ribulose-phosphate 3-epimerase, but these are not limited thereto. In the domain in which first beta-sheet structure-coil structure-alpha-helix structure-second beta-sheet structure are connected, the first amino acid residue of the motif III may start at the C-terminus of the first beta-sheet, and the domain may be included in the binding site or may have a structure in which some regions overlap, and the domain may be identical to the domain including the motif I (FIG. 1).

More specifically the motifs II and III may be motifs included in the same location, when aligned in the enzyme of the present disclosure, but are not limited thereto.

Specifically, X may include any amino acid without limitation, and specifically threonine (T), alanine (A), methionine (M), leucine (L), valine (V), asparagine (N), or isoleucine (I), but is not limited thereto.

Further, X' may include any amino acid, except for aspartic acid (D), without limitation, and specifically an uncharged amino acid or a positively charged amino acid. Specifically, the uncharged amino acid may include all of polar amino acids and non-polar amino acids, and may be any one of serine, threonine, cysteine, asparagine, glutamine, glycine, alanine, proline, valine, leucine, isoleucine, and methionine. Further, the positively charged amino acid may be any one of lysine, arginine, and histidine. For example, the positively charged amino acid may include asparagine (N) and lysine (K). More specifically the motif III may include a sequence of M-(T/A/M/L)-(V/N/I)-N-P-G, but is not limited thereto.

The enzyme of the present disclosure may further include a motif consisting of an amino acid sequence of the following SEQ ID NO: 4. It is apparent that a sequence including insertion, substitution, deletion, etc. of meaningless amino acid residues may also be included in the enzyme of the present disclosure, as long as it does not influence the activity of the amino acid sequence of SEQ ID NO: 4.

```
SEQ ID NO: 4:
S-X-M/I-C (X is any amino acid residue)
```

The motif having the amino acid sequence of SEQ ID NO: 4 may be included in the N-terminal region of the ribulose-phosphate 3-epimerase, but is not limited thereto. Specifically, the motif may be located at amino acid positions 5 to 20, and more specifically at amino acid positions 7 to 19 from the first amino acid of the N-terminus of the ribulose-phosphate 3-epimerase, but is not limited thereto. In other words, serine (S), which is the first amino acid residue of the motif having the amino acid sequence of SEQ ID NO: 4, may be located between positions 7 to 16, and cysteine (C), which is the last residue of the motif having the amino acid sequence of SEQ ID NO: 4, may be located between positions 10 to 19 from the first amino acid of the N-terminus of the ribulose-phosphate 3-epimerase, but these are not limited thereto. Further, the motif of SEQ ID NO: 4 may be formed after the beta-sheet structure, and specifically a part of the motif sequence of SEQ ID NO: 4 may be included in the alpha-helix structure formed after the beta-sheet structure.

Specifically, X may include any amino acid without limitation, specifically methionine, isoleucine, leucine, or valine, but is not limited thereto. More specifically the motif consisting of the amino acid sequence of SEQ ID NO: 4 may include a sequence of SIMC (SEQ ID NO: 27), SMMC (SEQ ID NO: 28), SLMC (SEQ ID NO: 29), or SVMC (SEQ ID NO: 30), but is not limited thereto.

The enzyme of the present disclosure may further include a motif consisting of an amino acid sequence of the following SEQ ID NO: 5. It is apparent that a sequence including insertion, substitution, deletion, etc. of meaningless amino acid residues may also be included in the enzyme of the present disclosure, as long as it does not influence the activity of the amino acid sequence of SEQ ID NO: 5.

```
SEQ ID NO: 5:
G-X-X-X-X-F/L (X is any amino acid residue)
```

The motif consisting of the amino acid sequence of SEQ ID NO: 5 may be included in the C-terminal region of the ribulose-phosphate 3-epimerase, but is not limited thereto. Specifically, the motif may be located at amino acid positions 190 to 210, and more specifically at amino acid positions 196 to 210 from the first amino acid of the N-terminus of the ribulose-phosphate 3-epimerase, but is not limited thereto. In other words, glycine (G), which is the first amino acid residue of the motif consisting of the amino acid sequence of SEQ ID NO: 5, may be located between positions 196 to 205, and phenylalanine (F), which is the last residue of the motif consisting of the amino acid sequence of SEQ ID NO: 5, may be located between positions 201 to 210 from the first amino acid of the N-terminus of the ribulose-phosphate 3-epimerase, but these are not limited thereto. Further, the motif of SEQ ID NO: 5 may be formed after the beta-sheet structure, and specifically a part of the motif sequence of SEQ ID NO: 5 may be included in the alpha-helix structure formed after the beta-sheet structure.

Specifically, each X in the motif consisting of the amino acid sequence of SEQ ID NO: 5 may independently be threonine, serine, glycine, leucine, cysteine, isoleucine, asparagine, lysine, alanine, valine, or glutamine, but is not limited thereto. More specifically the motif consisting of the amino acid sequence of SEQ ID NO: 5 may include an amino acid sequence of GNSGLF (SEQ ID NO: 31), GSSGLFGSSSLF (SEQ ID NO: 32), GSTSLF (SEQ ID NO: 33), GTAGLF (SEQ ID NO: 34), GTKGLF (SEQ ID NO: 35), GTQSLF (SEQ ID NO: 36), GTSCLF (SEQ ID NO: 37), GTSGLF (SEQ ID NO: 38), GTSSIF (SEQ ID NO: 39), GTSGIF (SEQ ID NO: 40), GTSSLF (SEQ ID NO: 41), or GTSSVF (SEQ ID NO: 42), but is not limited thereto. The enzyme of the present disclosure is characterized in that it has high activity of converting fructose-6-phosphate to psicose-6-phosphate by including the motif(s) of SEQ ID NO(s): 4 and/or 5.

The respective amino acid residues included in the motif of the present disclosure may be independently combined with each other to constitute the motif.

The ribulose-phosphate 3-epimerase of the present disclosure may not include a specific motif, i.e., motif II, thereby exhibiting very low psicose 3-epimerization activity, indicating that a final product psicose may be obtained with a high yield by reducing a side reaction during the process of preparing psicose-6-phosphate from fructose-6-phosphate. Further, the ribulose-phosphate 3-epimerase may be used in combination with other enzymes (e.g., psicose-6-phosphate phosphatase) to be effectively applied to psicose production.

The alpha-helix (α-helix) structure, beta-sheet (β-sheet) structure, and coil structure of the present disclosure may be understood as a common definition as mentioned in Kwang-soo Kim et al. (Crystal Structure of d-Psicose 3-epimerase from *Agrobacterium tumefaciens* and its Complex with True Substrate d-Fructose, Volume 361, Issue 5, 1 Sep. 2006, Pages 920-931), etc., and the alpha-helix may be a right-handed alpha-helix. The structure may be obtained by direct prediction by way of a commonly known method such as NMR, X-ray crystallography, etc., or by using Rosetta or web server (I-TASSER, ROBETTA, etc.) based on the amino acid sequence.

Further, in the present disclosure, a domain in which the structures are assembled may be expressed as structure1-structure2.

Further, the ribulose-phosphate 3-epimerase of the present disclosure may be derived from any one selected from the group consisting of *Chthonomonas, Geobacillus, Mahella, Thermoanaerobacterium, Tepidanaerobacter, Ardenticatenia, Firmicutes, Aenbacillus, Epulopiscium*, and *Thermoflavimicrobium*, and more specifically may be derived from any one selected from the group consisting of *Chthonomonas calidirosea* T49, *Geobacillus* sp. 8, *Geobacillus thermocatenulatus*, *Mahella australiensis* 50-1 BON, *Thermoanaerobacterium* sp. PSU-2, *Thermoanaerobacterium thermosaccharolyticum*, *Tepidanaerobacter syntrophicus*, *Ardenticatenia bacterium, Firmicutes bacterium* HGW-Firmicutes-5. *Aeribacillus pallidus, Epulopiscium* sp. SCG-B05WGA-EpuloA1, and *Thermoflavimicrobium dichotomicum*, but is not limited thereto.

Further, the ribulose-phosphate 3-epimerase of the present disclosure may include any one sequence selected from the group consisting of amino acid sequences of SEQ ID NO: 15 to 26, or may consist of any one sequence selected from the group consisting of amino acid sequences of SEQ ID NO: 15 to 26, but is not limited thereto. More specifically the enzyme may consist of the amino acid sequence of SEQ ID NO: 19, 20, or 22, but is not limited thereto.

In the ribulose-phosphate 3-epimerase of the present disclosure, the presence or absence of the specific motif has an important effect on the enzyme activity, and thus the enzyme sequence excluding the motif region may have low identity between sequences. Specifically, the enzyme may consist of any one sequence selected from the group consisting of amino acid sequences having 26%, 40%, 45%, 50%, 55%, 60%, 65%, 70%, 75%, 80%, 85%, 90%, 95%, 96%, 97%, 98%, or 99% or more sequence identity to the region excluding the motifs I and III in the amino acid sequence, and amino acid sequences having 24%, 40%, 45%, 50%, 55%, 60%, 65%, 70%, 75%, 80%, 85%, 90%, 95%, 96%, 97%, 98%, or 99% or more sequence identity to the region excluding the motifs I and III, and the regions of SEQ ID NOs: 4 and 5, but is not limited thereto.

Further, the enzyme may include any one amino acid sequence of SEQ ID NOs: 15 to 26 or an amino acid sequence having 70% or more homology or identity thereto, but is not limited thereto. Specifically, the amino acid sequence may include the sequences of SEQ ID NOs: 15 to 26 and amino acid sequences having at least 70%, 75%, 80%, 85%, 90%, 95%, 96%, 97%, 98%, or 99% or more homology or identity to the sequences. Further, it is obvious that a protein having an amino acid sequence with deletion, modification, substitution, or addition in part of the sequence may also be included within the scope of the present disclosure, as long as the amino acid sequence has such homology or identity and exhibits efficacy corresponding to that of the protein.

In other words, even though a "protein having an amino acid sequence listed with a specific sequence number" is disclosed in the present disclosure, as long as a protein has an activity the same as or equivalent to that of the protein consisting of the amino acid sequence of the corresponding sequence number, it is apparent that proteins having an amino acid sequence which is partially deleted, modified, substituted, conservatively substituted, or added are also included in the scope of the present disclosure. For example, when the protein has activity the same as or equivalent to that of the enzyme, it is apparent that addition of a sequence which does not modify a function of the protein before and after the amino acid sequence, naturally occurring mutation, silent mutation thereof, or conservative substitution are not excluded, and the sequence addition or mutation is included in the scope of the present disclosure.

As used herein, the term "homology" or "identity" refers to the degree of relevance between two given amino acid sequences or nucleotide sequences, and may be expressed as a percentage.

The terms "homology" and "identity" may be often used interchangeably with each other.

The sequence homology or identity of conserved polynucleotides or polypeptides may be determined by standard alignment algorithms, and may be used together with a default gap penalty established by the program being used. Substantially, homologous or identical sequences are generally expected to hybridize to all or at least about 50%, about 60%, about 70%, about 80%, or about 90% or more of the entire length of the sequences under moderate or highly stringent conditions. Polynucleotides that include degenerate codons instead of codons in the hybridizing polynucleotides are also considered.

Whether any two polynucleotide or polypeptide sequences have homology, similarity, or identity may be determined using a known computer algorithm such as the "FASTA" program as in Pearson et al (1988) *Proc. Natl. Acad. Sci. USA* 85:2444 using default parameters. Alternatively, it may be determined by the Needleman-Wunsch algorithm (Needleman and Wunsch, 1970, *J. Mol. Biol.*

48:443-453), which is performed using the Needleman program of the EMBOSS package (EMBOSS: The European Molecular Biology Open Software Suite, Rice et al., 2000, *Trends Genet.* 16:276-277) (version 5.0.0 or later) (GCG program package (Devereux, J. et al., *Nucleic Acids Research* 12:387 (1984)), BLASTP. BLASTN, FASTA (Atschul, S. F. et al., *J MOLEC BIOL* 215:403 (1990); *Guide to Huge Computers*, Martin J. Bishop, ed., Academic Press, San Diego, 1994, and CARILLO et al. (1988) *SIAM J Applied Math* 48:1073). For example, the homology, similarity, or identity may be determined using BLAST or ClustalW of the National Center for Biotechnology Information.

The homology, similarity, or identity of polynucleotides or polypeptides may be determined by comparing sequence information using, for example, the GAP computer program, such as Needleman et al. (1970), *J Mol Biol.* 48:443 as disclosed in Smith and Waterman, *Adv. Appl Math* (1981) 2:482. Briefly, the GAP program defines the homology, similarity, or identity as a value obtained by dividing the number of similarly aligned symbols (i.e., nucleotides or amino acids) by the total number of the symbols in the shorter of the two sequences. Default parameters for the GAP program may include (1) a unary comparison matrix (containing a value of 1 for identities and 0 for non-identities) and the weighted comparison matrix of Gribskov et al. (1986) *Nucl. Acids Res.* 14:6745, as disclosed in Schwartz and Dayhoff, eds., *Atlas Of Protein Sequence And Structure*, National Biomedical Research Foundation, pp. 353-358 (1979) (alternatively, a substitution matrix of EDNAFULL (EMBOSS version of NCBI NUC4.4); (2) a penalty of 3.0 for each gap and an additional 0.10 penalty for each symbol in each gap (or a gap opening penalty of 10 and a gap extension penalty of 0.5); and (3) no penalty for end gaps. Accordingly, as used herein, the term "homology" or "identity" refers to the relatedness between sequences.

Meanwhile, the ribulose-phosphate 3-epimerase of the present disclosure may have heat resistance, but is not limited thereto.

As used herein, the term "heat resistance" means a property capable of exhibiting the original activity of an enzyme without losing its activity even in a high-temperature environment, and heat resistance of an enzyme has various advantages in a process of producing a desired product. Specifically, the ribulose-phosphate 3-epimerase of the present disclosure may have psicose-6-phosphate 3-epimerization activity at 40° C. or higher, more specifically at 50° C. or higher, and much more specifically at 60° C. or higher, but is not limited thereto. Even much more specifically the enzyme of the present disclosure may have psicose-6-phosphate 3-epimerization activity under conditions of pH 5.0 to 10.0 and 50° C. to 90° C. for 1 minute to 24 hours, but is not limited thereto.

The ribulose-phosphate 3-epimerase of the present disclosure may be obtained by transforming the enzyme itself or DNA expression the enzyme into a strain, culturing the strain to obtain a culture, disrupting the culture, and then purifying the product through a column, etc. The strain for transformation may be *Escherichia coli, Corynebacterium glutamicum, Aspergillus oryzae, Saccharomyces cerevisiae, Yarrowia lipolytica, Pichia pastoris*, or *Bacillus subtilis*, but is not limited thereto, and may be potentially transformed into a GRAS (Generally Recognized as Safe) strain in the future.

A method of purifying the ribulose-phosphate 3-epimerase of the present disclosure is not particularly limited, and a method commonly used in the art of the present disclosure may be used. Non-limiting examples thereof may include chromatography, heat treatment, adsorption, filtration, ion purification, etc. Only one of the purification methods may be performed, and two or more thereof may be used in combination.

Another aspect of the present disclosure provides a nucleic acid encoding the ribulose-phosphate 3-epimerase, or a vector including the nucleic acid.

As used herein, the "nucleic acid" has a meaning which collectively includes DNA or RNA molecules. Nucleotides which are the basic structural units in nucleic acids may include not only natural nucleotides but also modified analogs thereof in which sugar or base moieties are modified.

The nucleic acid of the present disclosure may be a DNA or RNA sequence, in which the unit nucleotides are linked to each other via covalent bonds, and specifically it may be any one of all possible nucleotide sequences at the time of DNA conversion from the amino acid sequences of SEQ ID NOs: 15 to 26 (amino acids are changed to 61 codons), and more specifically it may include a nucleic acid having 90% or more, 95% or more, 97% or more, 99% or more, or 100% homology, similarity, or identity to each nucleotide which may be translated to any one amino acid sequence of the amino acid sequences of SEQ ID NOs: 15 to 26 of the present disclosure while capable of exhibiting desired enzymatic activity when translated. It is also obvious that a polynucleotide which may be translated, due to codon degeneracy, into a protein having the same activity or the same amino acid sequence after translation, specifically consisting of any one amino acid sequence of SEQ ID NOs: 15 to 26, or a protein having homology, similarity, or identity thereto may also be included in the scope of the present disclosure. More specifically the sequence of the nucleic acid of the present disclosure is not separately indicated, and the nucleic acid may consist of any number of DNA codons which may be translated into the amino acid sequences of SEQ ID NOs: 15 to 26, but is not limited thereto.

Alternatively, a probe which may be prepared from a known gene sequence, for example, any sequence which hybridizes with a sequence complementary to all or a part of the nucleotide sequence under stringent conditions to encode the enzyme of the present disclosure, may be included without limitation.

The "stringent conditions" refer to conditions which allow the specific hybridization between the polynucleotides. Such conditions are specifically disclosed in the literature (e.g., J. Sambrook et al., supra). For example, the stringent conditions may include conditions under which genes having high homology or identity, homology or identity of 80% or more, or 85% or more, specifically 90% or more, more specifically 95% or more, even more specifically 97% or more, and particularly specifically 99% or more hybridize with each other, while genes having homology or identity lower than the above homology or identity do not hybridize with each other; or may include ordinary washing conditions of Southern hybridization, i.e., washing once, specifically two or three times, at a salt concentration and a temperature corresponding to 60° C., 1×SSC, 0.1% SDS, specifically 60° C., 0.1×SSC, 0.1% SDS, and more specifically 68° C., 0.1× SSC, 0.1% SDS.

Hybridization requires that two polynucleotides have complementary sequences, although mismatches between bases are possible depending on the stringency of the hybridization. The term "complementary" is used to describe the relationship between nucleotide bases that may hybridize with each other. For example, with respect to DNA, adenosine is complementary to thymine, and cytosine is complementary to guanine. Therefore, the present disclosure may also include an isolated nucleic acid fragment complementary to the entire sequence as well as a nucleic acid sequence substantially similar thereto.

Specifically, the polynucleotide having homology or identity may be detected using hybridization conditions including a hybridization step at a $T_m$ value of 55° C. under the above-described conditions. Additionally, the $T_m$ value may be 60° C. 63° C., or 65° C. but is not limited thereto, and may be appropriately controlled by those skilled in the art depending on the purpose thereof.

The appropriate stringency for hybridizing polynucleotides depends on the length and degree of complementarity of the polynucleotides, and these variables are well known in the art.

As used herein, the term "vector" refers to a DNA construct including a nucleotide sequence of a nucleic acid encoding the enzyme of the present disclosure, which is operably linked to a suitable expression regulatory sequence to express the desired variant protein in a suitable host. The regulatory sequence includes a promoter capable of initiating transcription, any operator sequence for regulating such transcription, a sequence encoding a suitable mRNA ribosome binding site, and a sequence for regulating the termination of transcription and translation. The vector may be transformed into an appropriate host cell, and then may replicate or function regardless of a host genome or may be integrated into the genome itself.

The vector used in the present disclosure is not particularly limited, as long as it is replicable in a host cell, and any vector known in the art may be used. Examples of vectors to be generally used may include native or recombinant plasmids, cosmids, viruses, and bacteriophages. For example, as the phage vector or the cosmid vector, pWE15, M13, MBL3, MBL4, IXII, ASHII, APII, t10, t11, Charon4A, Charon21A, etc. may be used, and as the plasmid vector, pBR-based, pUC-based, pBluescriptII-based, pGEM-based, pTZ-based, pCL-based, pET-based plasmids, etc. may be used. Specifically, pDZ, pACYC177, pACYC184, pCL, pECCG117, pUC19, pBR322, pMW118, pCC1BAC vector, etc. may be used.

Still another aspect of the present disclosure provides a transformant including the nucleic acid encoding the enzyme of the present disclosure or the vector including the nucleic acid encoding the enzyme of the present disclosure.

As used herein, the "transformant including the nucleic acid encoding the enzyme" or the "transformant including the vector including the nucleic acid encoding the enzyme" may refer to a microorganism recombined to express the ribulose-phosphate 3-epimerase of the present disclosure, and for example, refers to a host cell or microorganism which may include the nucleic acid encoding the ribulose-phosphate 3-epimerase or may be transformed with the vector including the nucleic acid encoding the ribulose-phosphate 3-epimerase to express the ribulose-phosphate 3-epimerase. With respect to the objects of the present disclosure, the ribulose-phosphate 3-epimerase expressed by the transformant may consist of any one amino acid sequence of SEQ ID NOs: 15 to 26, but is not limited thereto.

As used herein, the "transformation" refers to introduction of the vector including the nucleic acid encoding the ribulose-phosphate 3-epimerase of the present disclosure into a host cell in such a way that the protein encoded by the nucleic acid is expressed in the host cell. As long as the transformed nucleic acid may be expressed in the host cell, all transformed nucleic acids may be included regardless of whether the transformed nucleic acid is inserted and located in a chromosome of the host cell or located outside the chromosome. In addition, the nucleic acid includes DNA and RNA encoding the nucleic acid encoding the ribulose-phosphate 3-epimerase of the present disclosure. The nucleic acid may be introduced in any form as long as the nucleic acid may be introduced into a host cell to be expressed. For example, the nucleic acid may be introduced into a host cell in a form of an expression cassette, which is a genomic structure including all elements required for autonomous expression. The expression cassette may generally include a promoter which is operably linked to the nucleic acid, a transcription termination signal, a ribosome binding site, and a translation termination signal. The expression cassette may be a self-replicable expression vector. Further, the nucleic acid may also be introduced into the host cell as it is, and may be operably linked to a sequence required for expression in the host cell, but is not limited thereto.

In addition, the term "operably linked" means that the gene sequence is functionally linked to a promoter sequence, which initiates and mediates the transcription of the nucleic acid encoding the psicose-6-phosphate phosphatase of the present disclosure.

The insertion of the nucleic acid or the vector into the chromosome may be performed by way of any method known in the art, for example, homologous recombination, but is not limited thereto. A selection marker for confirming the chromosomal insertion may be further included. The selection marker is to select cells transformed by the vector, i.e., to confirm insertion of a target nucleic acid molecule. Markers providing selective phenotypes such as drug resistance, auxotrophy, resistance to cytotoxic drugs, or expression of surface-modified proteins may be used. In an environment treated with a selective agent, since only cells expressing the selection marker survive or represent different phenotypes, transformed cells may be selected.

A method of transforming the vector of the present disclosure includes any method of introducing a nucleic acid into a cell, and may be carried out by selecting a suitable standard technique known in the art depending on the host cell. Examples of the method may include electroporation, calcium phosphate ($CaPO_4$) precipitation, calcium chloride ($CaCl_2$)) precipitation, retroviral infection, microinjection, a polyethyleneglycol (PEG) technique, a DEAE-dextran technique, a cationic liposome technique, a lithium acetate-DMSO technique, etc., but are not limited thereto.

As the host cell, it is preferable to use a host having a high efficiency of introducing DNA into a host cell and a high efficiency of expressing the introduced DNA. For example, it may be a *Corynebacterium* sp. microorganism, an *Escherichia* sp. microorganism, a *Serratia* sp. microorganism, a *Bacillus* sp. microorganism, a *Saccharomyces cerevisiae* sp. microorganism, or a *Pichia* sp. microorganism, and specifically *E. coli*, but is not limited thereto. All GRAS strains are applicable.

More specifically the transformant of the present disclosure may be *E. coli* BL21(DE3)/pET-CJ-ef7, *E. coli* BL21(DE3)/pET-CJ-ef12, or *E. coli* BL21(DE3)/pET-CJ-ef15, but is not limited thereto.

Still another aspect of the present disclosure provides a composition for producing psicose-6-phosphate, the composition including the ribulose-phosphate 3-epimerase, the microorganism expressing the ribulose-phosphate 3-epimerase, or a culture of the microorganism.

The composition for producing psicose-6-phosphate of the present disclosure may include the ribulose-phosphate 3-epimerase exhibiting activity of converting fructose-6-phosphate to psicose-6-phosphate, the microorganism expressing the ribulose-phosphate 3-epimerase, or the culture of the microorganism, and thus when the composition is brought into contact (reacted) with fructose-6-phosphate, psicose-6-phosphate may be produced from the fructose-6-phosphate.

Specifically, the composition may further include fructose-6-phosphate as a substrate, but is not limited thereto.

The composition for producing psicose-6-phosphate of the present disclosure may further include any suitable excipient commonly used in the composition for producing psicose-6-phosphate. The excipient may include, for example, a preservative, a wetting agent, a dispersing agent, a suspending agent, a buffer, a stabilizing agent, an isotonic agent, etc., but is not limited thereto.

The composition for producing psicose-6-phosphate of the present disclosure may further include a metal ion or a metal salt. In one embodiment, the metal ion may be a divalent cation, and specifically one or more metal ions selected from the group consisting of Ni, Mg, Ni, Co, Mn, Fe and Zn. More specifically the composition for producing psicose-6-phosphate of the present disclosure may further include a metal salt. Even more specifically the metal salt may be one or more selected from the group consisting of $NiSO_4$, $MgSO_4$, $MgCl_2$, $NiCl_2$, $CoSO_4$, $CoCl_2$, $MnCl_2$, $MnSO_4$, $FeSO_4$, and $ZnSO_4$.

Still another aspect of the present disclosure provides a method of producing psicose-6-phosphate, the method including the step of bringing fructose-6-phosphate into contact with the ribulose-phosphate 3-epimerase, the microorganism expressing the ribulose-phosphate 3-epimerase, or the culture of the microorganism.

The ribulose-phosphate 3-epimerase of the present disclosure may exhibit activity of converting fructose-6-phosphate to psicose-6-phosphate, and therefore, when the ribulose-phosphate 3-epimerase, the microorganism expressing the same, or the culture of the microorganism is brought into contact with fructose-6-phosphate, psicose-6-phosphate may be produced from fructose-6-phosphate.

The conditions for contacting and reacting with fructose-6-phosphate and psicose-6-phosphate may be appropriately selected by those skilled in the art by considering the substrate, enzyme, etc.

Specifically, the step of producing psicose-6-phosphate by bringing fructose-6-phosphate into contact with the ribulose-phosphate 3-epimerase may be performed at pH 5.0 to 9.0 and at a temperature of 40° C. to 80° C., and/or for 2 hours to 24 hours, more specifically at pH 6.0 to 8.0 and at a temperature of 40° C. to 60° C., and/or for 20 hours to 24 hours, and more specifically at pH 7.0 and a temperature of 50° C. for 24 hours, but is not limited thereto.

The method of producing psicose-6-phosphate of the present disclosure may further include the step of obtaining and/or purifying the prepared psicose-6-phosphate, but is not limited thereto.

The step of obtaining and/or purifying psicose-6-phosphate may be performed by way of a method known in the art, but is not limited to a particular method.

Still another aspect of the present disclosure provides a composition for producing psicose, the composition including the ribulose-phosphate 3-epimerase, the microorganism expressing the ribulose-phosphate 3-epimerase, or the culture of the microorganism. Specifically, the composition may further include fructose-6-phosphate as a substrate, but is not limited thereto.

The composition for producing psicose of the present disclosure may produce psicose by further including an enzyme needed to produce psicose, e.g., psicose-6-phosphate phosphatase which produces psicose by dephosphorylation of phosphate from psicose-6-phosphate, in addition to the ribulose-phosphate 3-epimerase which produces psicose-6-phosphate from fructose-6-phosphate.

Specifically, the composition for producing psicose of the present disclosure may further include one or more enzymes selected from the group consisting of glucose-6-phosphate isomerase, phosphoglucomutase, polyphosphate glucokinase, α-glucan phosphorylase, starch phosphorylase, maltodextrin phosphorylase or sucrose phosphorylase, α-amylase, pullulanase, isoamylase, α-glucanotransferase, glucoamylase, sucrase, and psicose-6-phosphate phosphatase, a microorganism expressing the same, or a culture of the microorganism, and specifically may further include psicose-6-phosphate phosphatase, but is not limited thereto.

More specifically the composition for producing psicose of the present disclosure may further include (a) (i) starch, maltodextrin, sucrose, or a combination thereof, glucose, glucose-1-phosphate, glucose-6-phosphate, or fructose-6-phosphate: (ii) phosphate; (iii) psicose-6-phosphate phosphatase: (iv) glucose-6-phosphate-isomerase; (v) phosphoglucomutase or glucokinase; and/or (vi) α-glucan phosphorylase, starch phosphorylase, maltodextrin phosphorylase, sucrose phosphorylase, α-amylase, pullulanase, isoamylase, glucoamylase, or sucrase; or (b) a microorganism expressing the enzyme of (a) or a culture of the microorganism expressing the enzyme of (a), but is not limited thereto.

However, this is for illustrative purposes only, and as long as psicose may be produced using the ribulose-phosphate 3-epimerase of the present disclosure, the enzymes included in the composition for producing psicose of the present disclosure and the substrate used for psicose production are not limited.

Specifically, starch/maltodextrin phosphorylase (EC 2.4.1.1) and α-glucan phosphorylase of the present disclosure may include any protein, as long as it is a protein having activity of producing glucose-1-phosphate from starch or maltodextrin by phosphoryl transfer of phosphate to glucose. The starch/maltodextrin phosphorylase (EC 2.4.1.1) and α-glucan phosphorylase may include any protein, as long as it is a protein having activity of producing glucose-1-phosphate from starch or maltodextrin by phosphoryl transfer of phosphate to glucose. The sucrose phosphorylase (EC 2.4.1.7) may include any protein, as long as it is a protein having activity of producing glucose-1-phosphate from sucrose by phosphoryl transfer of phosphate to glucose. The α-amylase (EC 3.2.1.1), pullulanase (EC 3.2.1.41), isoamylase (EC 3.2.1.68), 4-α-glucanotransferase (EC 2.4.1.25), and glucoamylase (EC 3.2.1.3) which are starch-degrading enzymes may include any protein, as long as it is a protein having activity of converting starch or maltodextrin to debranched maltooligosaccharide or glucose. The sucrase (EC 3.2.1.26) may include any protein, as long as it is a protein having activity of converting sucrose to glucose. The phosphoglucomutase (EC 5.4.2.2) of the present disclosure may include any protein, as long as it is a protein having activity of converting glucose-1-phosphate to glucose-6-phosphate. The polyphosphate glucokinase (EC 2.7.1.63) may include any protein, as long as it is a protein having activity of converting glucose to glucose-6-phosphate by transferring a phosphate of polyphosphate to glucose. The glucose-6-phosphate-isomerase of the present disclosure may include any protein, as long as it is a protein having activity of converting glucose-6-phosphate to fructose-6-phosphate. The psicose-6-phosphate phosphatase of the present disclosure may include any protein, as long as it is a protein having activity of converting psicose-6-phosphate to psicose. More specifically the psicose-6-phosphate phosphatase may be a protein having activity of irreversibly converting psicose-6-phosphate to psicose.

The enzymes included in the composition for producing psicose of the present disclosure may exhibit a high psicose conversion rate in a one-pot enzymatic conversion in which a plurality of enzymes and substrates are used at the same time.

The composition for producing psicose of the present disclosure may further include any suitable excipient commonly used in the composition for producing psicose. The excipient may include, for example, a preservative, a wetting agent, a dispersing agent, a suspending agent, a buffer, a stabilizing agent, an isotonic agent, etc., but is not limited thereto.

The composition for producing psicose of the present disclosure may further include a metal ion or a metal salt. In one embodiment, the metal ion may be a divalent cation, and specifically one or more metal ions selected from the group consisting of Ni, Mg, Ni, Co, Mn, Fe, and Zn. More specifically the composition for producing psicose of the present disclosure may further include a metal salt, and even more specifically the metal salt may be one or more selected from the group consisting of $NiSO_4$, $MgSO_4$, $MgCl_2$, $NiCl_2$, $CoSO_4$, $CoCl_2$, $MnCl_2$, $MnSO_4$, $FeSO_4$, and $ZnSO_4$.

Still another aspect of the present disclosure provides a method of producing psicose, the method including the step of bringing fructose-6-phosphate into contact with the ribulose-phosphate 3-epimerase, the microorganism expressing the ribulose-phosphate 3-epimerase, or the culture of the microorganism.

Specifically, the method of producing psicose of the present disclosure may sequentially include the steps of:

bringing fructose-6-phosphate into contact with the ribulose-phosphate 3-epimerase, the microorganism expressing the ribulose-phosphate 3-epimerase, or the culture of the microorganism expressing the ribulose-phosphate 3-epimerase to convert the fructose-6-phosphate to psicose-6-phosphate; and bringing psicose-6-phosphate into contact with the psicose-6-phosphate phosphatase, the microorganism expressing the psicose-6-phosphate phosphatase, or the culture of the microorganism to convert the psicose-6-phosphate to psicose, but is not limited thereto.

Further, the method of producing psicose of the present disclosure may further include the step of bringing glucose-6-phosphate into contact with the glucose-6-phosphate-isomerase, the microorganism expressing the glucose-6-phosphate-isomerase, or the culture of the microorganism expressing the glucose-6-phosphate-isomerase to convert the glucose-6-phosphate to fructose-6-phosphate, before the step of converting fructose-6-phosphate to psicose-6-phosphate.

The method of producing psicose of the present disclosure may further include the step of bringing glucose-1-phosphate into contact with the phosphoglucomutase, the microorganism expressing the phosphoglucomutase, or the culture of the microorganism expressing the phosphoglucomutase to convert the glucose-1-phosphate to glucose-6-phosphate, before the step of converting glucose-6-phosphate to fructose-6-phosphate.

The method of producing psicose of the present disclosure may further include the step of bringing glucose into contact with the polyphosphate glucokinase, the microorganism expressing the polyphosphate glucokinase, or the culture of the microorganism expressing the polyphosphate glucokinase, and polyphosphate to convert the glucose to glucose-6-phosphate, before the step of converting glucose-6-phosphate to fructose-6-phosphate.

The method of producing psicose of the present disclosure may further include the step of bringing starch, maltodextrin, sucrose, or a combination thereof into contact with α-glucan phosphorylase, starch phosphorylase, maltodextrin phosphorylase, or sucrose phosphorylase; the microorganism expressing the phosphorylase; or the culture of the microorganism expressing the phosphorylase, and phosphate to convert the starch, maltodextrin, sucrose, or a combination thereof to glucose-1-phosphate, before the step of converting glucose-1-phosphate to glucose-6-phosphate.

The method of producing psicose of the present disclosure may further include the step of bringing starch, maltodextrin, sucrose, or a combination thereof into contact with α-amylase, pullulanase, isoamylase, glucoamylase, or sucrase; the microorganism expressing the α-amylase, pullulanase, glucoamylase, sucrase, or isoamylase: or the culture of the microorganism expressing the α-amylase, pullulanase, glucoamylase, sucrase, or isoamylase to convert the starch, maltodextrin, sucrose, or a combination thereof to glucose, before the step of converting starch, maltodextrin, sucrose or a combination thereof to glucose-1-phosphate.

The ribulose-phosphate 3-epimerase, psicose-6-phosphate phosphatase, α-glucan phosphorylase, phosphoglucomutase (or phosphomannomutase), glucose-6-phosphate isomerase, psicose-6-phosphate 3-epimerase (or ribulose-5-phosphate 3-epimerase), pullulanase (or isoamylase), 4-α-glucanotransferase, polyphosphate glucokinase, etc. used in the method of producing psicose of the present disclosure may have no side reactivity or less side reactivity to the final product psicose.

The method of producing psicose of the present disclosure decomposes a high concentration of starch to produce the optimum/maximum psicose in a complex combination with glucose phosphate converting enzymes. To secure the maximum productivity of psicose, up to eight kinds of enzymes may be used in combination.

First, glucan phosphorylase (glycogen phosphorylase, EC 2.4.1.1), which is an enzyme that degrades starch and produces glucose-1-phosphate, is specific to α-1,4 linked starch to produce glucose-1-phosphate. Second, phosphoglucomutase (EC 2.7.5.1) or phosphomannomutase (EC 5.4.2.8), which converts glucose-1-phosphate thus produced to glucose-6-phosphate, is used in the intermediate complex enzymatic reaction. Third, glucose-6-phosphate isomerase (EC 5.3.1.9), which is an enzyme that converts glucose-6 phosphate to fructose-6-phosphate, is used. Fourth, fructose-6-phosphate 3-epimerase, which is an enzyme that converts fructose-6-phosphate to psicose-6-phosphate, is used to produce psicose-6-phosphate in a reversible reaction.

Additionally, to increase the starch utilization rate, pullulanase (EC 3.2.1.41) or isoamylase (EC 3.2.1.68) enzyme is also used to degrade branch linkages of α-1,6 linkage in addition to α-1,4 linkage of amylopectin. Further, to increase the starch utilization of glucan phosphorylase, glucanotransferase (4-alpha-glucanotransferase, EC 2.4.1.25) may be used. By binding oligosaccharides in the form of α-1,4 linkage to maltose or other oligosaccharides which are substrates with relatively low activity, the utilization rate of segmented starch substrates may be increased. Additionally, additional psicose production is possible using polyphosphate glucokinase (polyphosphate-glucose phosphotransferase, EC 2.7.1.63) through a complex enzymatic reaction of the degraded glucose resulting from utilizing starch.

Further, in the method of producing psicose of the present disclosure, the contacting of the present disclosure may be performed at pH 5.0 to 9.0, specifically at pH 6.0 to 8.0.

In the method of producing psicose of the present disclosure, the contacting of the present disclosure may be performed at a temperature of 40° C. to 80° C. specifically at a temperature of 40° C. to 60° C. or 50° C. to 60° C.

In the method of producing psicose of the present disclosure, the contacting of the present disclosure may be performed for 2 hours to 24 hours, specifically 6 hours to 24 hours.

In the method of producing psicose of the present disclosure, the contacting of the present disclosure may be performed at pH 5.0 to 9.0 and at a temperature of 40° C. to 80° C., and/or for 2 hours to 24 hours. Specifically, the contacting may be performed at pH 6.0 to 8.0 and at a temperature of 40° C. to 60° C. or 50° C. to 60° C., and/or for 6 hours to 24 hours.

The method of producing psicose of the present disclosure may further include the step of purifying psicose. The purification of the present disclosure is not particularly limited, and may be performed using a method commonly used in the art of the present disclosure. Non-limiting examples thereof may include chromatography, fractional crystallization, ion purification, etc. These purification methods may be performed alone or in combination of two or more thereof. For example, the psicose product may be purified through chromatography, and isolation of sugars by chromatography may be performed using a difference in a weak binding force between the sugars to be isolated and metal ions bound to an ion resin.

In addition, the present disclosure may further include performing destaining, desalting, or both before or after the purification step of the present disclosure. By performing the destaining and/or desalting, a more purified psicose product without impurities may be obtained.

Hereinafter, the present disclosure will be described in more detail with reference to exemplary embodiments. However, these exemplary embodiments are only for better understanding of the present disclosure, and the scope of the present disclosure is not intended to be limited thereto.

In the present disclosure, amino acids may be represented by the following abbreviations or amino acid names:

TABLE 1

| Kind of amino acid | Abbreviation | DNA codon encoding corresponding amino acid | RNA codon encoding corresponding amino acid |
|---|---|---|---|
| alanine | A | GCT, GCC, GCA, GCG | GCU, GCC, GCA, GCG |
| arginine | R | AGA, AGG | AGA, AGG |
| asparagines | N | AAT, AAC | AAU, AAC |
| aspartic acid | D | GAT, GAC | GAU, GAC |
| cystein | C | TGT, TGC | UGU, UGC |
| glutamic acid | E | GAA, GAG | GAA, GAG |
| glutamine | Q | CAA, CAG | CAA, CAG |
| glycine | G | GGT, GGC, GGA, GGG | GGU, GGC, GGA, GGG |
| histidine | H | CAC, CAT | CAC, CAU |
| isoleucine | I | ATT, ATC, ATA | AUU, AUC, AUA |
| leucine | L | TTA, TTG, CTT, CTC, CTA, CTG | UUA, UUG, CUU, CUC, CUA, CUG |
| lycine | K | AAA, AAG | AAA, AAG |
| methionine | M | ATG | AUG |
| phenylalanine | F | TTT, TTC | UUU, UUC |
| proline | P | CCT, CCC, CCA, CCG | CCU, CCC, CCA, CCG |
| serine | S | TCT, TCC, TCA, TCG | UCU, UCC, UCA, UCG |
| threonine | T | ACT, ACC, ACA, ACG | ACU, ACC, ACA, ACG |
| tryptophan | W | TGG | UGG |
| tyrosine | Y | TAT, TAC | UAU, UAC |
| valine | V | GTT, GTC, GTA, GTG | GUU, GUC, GUA, GUG |

Example 1: Preparation of Recombinant Expression Vector of Each Enzyme and Transformed Microorganism To provide respective enzymes needed in the psicose production pathways of the present disclosure, genes of heat-resistant enzymes were selected. Additionally, for highly active epimerization activity, genes of enzymes having an amino acid sequence of S-X-M-C (SEQ ID NO: 4) or G-X-X-X-X-F (SEQ ID NO: 5) were selected (Table 2).

The selected genes of the amino acids were amplified by gene synthesis or by polymerase chain reaction (PCR) of each gene from genomic DNA of each strain, and each amplified DNA was inserted into a plasmid vector pET21a (NOVAGEN) for expression in E. coli using DNA assembly methods, and each recombinant expression vector was prepared. The expression vector was transformed into an E. coli BL21 (DE3) strain according to a common transformation method (Sambrook et al. 1989) to prepare each transformed microorganism.

Specifically, psicose-6-phosphate 3-epimerases of SEQ ID NOs: 6 to 26 were transformed into E. coli BL21(DE3) strain, respectively. Among them, the transformed microorganisms of SEQ ID NOs: 19, 20, and 22 by way of the above preparation method were deposited in the international depository authority. Korean Culture Center of Microorganisms (KCCM) on Apr. 16, 2019, with the Accession Nos. KCCM12494P (E. coli BL21(DE3)/pET-CJ-fep19), KCCM12495P (E. coli BL21(DE3)/pET-CJ-fep20), and KCCM12496P (E. coli BL21(DE3)/pET-CJ-fep22), respectively.

Example 2: Preparation of Recombinant Enzymes

To prepare recombinant enzymes, each transformed microorganism prepared in Example 1 was inoculated in a culture tube containing 5 mL of LB liquid medium, and a seed culture was performed in a shaking incubator at 37° C. until absorbance at 600 nm reached 2.0. The culture medium of the seed culture was inoculated in a culture flask containing an LB liquid medium to perform a main culture. When absorbance at 600 nm reached 2.0, 1 mM IPTG was added to induce expression and production of the recombinant enzyme. During the culturing process, an agitation speed was 180 rpm, and a culture temperature was maintained at 37° C. The culture medium was centrifuged at 8,000×g and 4° C. for 20 minutes to collect a cell pellet. The collected cell pellet was washed with 50 mM Tris-HCl (pH 8.0) buffer twice, and suspended in the same buffer, and cells were disrupted using a sonicator. The cell lysate was centrifuged at 13,000×g and 4° C. for 20 minutes to obtain only a supernatant. From the supernatant, the recombinant enzyme was purified using His-tag affinity chromatography, and dialyzed against 50 mM Tris-HCl (pH 8.0) buffer, and then used in reactions.

Example 3: Modeling of Psicose-6-Phosphate 3-Epimerase, Examination of Psicose 3-Epimerization Activity, and Comparison of Sequence Thereof An amino acid sequence of SEQ ID NO: 9, disclosed as ribulose-phosphate 3-epimerase, was input to 1-TASSER, Phyre2, Galaxyweb server to analyze a protein structure.

As a result, it was confirmed that the enzyme had a TIM-barrel fold, in which a β-sheet is located at the center and an α-helix structure surrounds it, and motifs I (V-D-G) and III (M-X-X-X'-P-G) in a structure (TIM-barrel fold), predicted as a psicose or psicose-6-phosphate binding site, were selected (FIG. 1, Blue dotted circle (motif I), Red dotted circle (motif III), example structure-model (SEQ ID NO: 9)).

Meanwhile, since the known psicose-6-phosphate 3-epimerases (ADL69228, WP_034772999, WP_029098887; WO2018/129275, WO2018/112139) exhibit activity of producing fructose by epimerization of psicose, a psicose production yield is reduced.

Accordingly, the present inventors predicted that aspartic acid (D) of (M-X-X-D-P-G) structurally having a negative charge may influence psicose 3-epimerization activity, and for this reason, enzymes predicted not to influence psicose 3-epimerization activity were selected (WP_085113038, PKM55438, WP_117016900), in which X' in the motif III (M-X-X-X'-P-G) is N/K having a different charge from aspartic acid.

As a result, it was confirmed that the psicose 3-epimerization activity may vary depending on the type of a specific motif in the enzyme.

Example 4: Examination of Psicose-6-Phosphate Conversion Activity of Ribulose-Phosphate 3-Epimerase To examine activity of ribulose-phosphate 3-epimerase of the present disclosure, which is an enzyme converting to psicose-6-phosphate, 50 mM fructose-6-phosphate or 20 mM glucose-1-phosphate was suspended in 50 mM Tris-HCl (pH 7.0) or 50 mM sodium-phosphate (pH 6-7) or 50 mM potassium-phosphate (pH 6-7) buffer, and the phosphoglucomutase or phosphomannomutase and glucose-6-phosphate isomerase and psicose-6-phosphate phosphatase and the recombinant ribulose-phosphate 3-epimerase prepared in Example 2 were added each in an amount of 0.1 unit/mL, and allowed to react at 45° C. to 70° C. for 1 hour to 24 hours.

To examine activity of psicose 3-epimerase, psicose was suspended at a concentration of 1% (w/v) in 50 mM Tris-HCl (pH 7.0) or 50 mM sodium-phosphate (pH 6-7) or 50 mM potassium-phosphate (pH 6-7) buffer, and 0.1 unit/mL of ribulose-phosphate 3-epimerase was added, and allowed to react at 45° C. to 70° C. for 1 hour to 24 hours. Production of glucose, fructose, or psicose was analyzed by HPLC. HPLC analysis was performed using an SP_0810 (Shodex) column and an Aminex HPX-87C (Bio-RAD) column at 80° C. using a mobile phase at a flow rate of 0.6 mL/min, and detection was performed using a refractive index detector (RID). Glucose, fructose, and psicose, which are general sugars each produced by mixing with the above enzymes, were qualitatively and quantitatively examined. For quantitative evaluation, a tolerance of the fructose conversion rate relative to the initial psicose concentration was set within 5% in consideration of spontaneous experimental error according to LC sensitivity, a fast substrate conversion rate, and a substrate concentration.

In Table 2, among several ribulose-phosphate 3-epimerases exhibiting the psicose-6-phosphate 3-epimerization activity, enzymes having no psicose 3-epimerization activity were divided, based on the presence or absence of M-X-X-N/K-P-G and V-D-G motifs. From the enzymes, an enzyme including a specific motif, specifically a motif of SEQ ID NO: 1 without a motif of SEQ ID NO: 2, and including a motif of SEQ ID NO: 3 in the same place instead of the motif of SEQ ID NO: 2 was confirmed to have high epimerization activity specific to psicose-6-phosphate. Further, as confirmed in sequences A and B, when the enzyme includes motifs I and III it has high epimerization activity specific to psicose-6-phosphate.

TABLE 2

| SEQ ID NO: | Genbank No. | Motif III (M-X-X-N/K-P-G) | Motif I (V-D-G) | Psicose 6 phosphate 3-epimerization activity | Psicose 3-epimerization activity |
|---|---|---|---|---|---|
| 6 | ADL69228 | X | X | Active | Active |
| 7 | WP_084772999 | X | X | | |
| 8 | WP_029098887 | X | 0 | | |
| 9 | KPL22606 | X | 0 | | |
| 10 | PNR87418 | X | 0 | | |
| 11 | PNR96608 | X | X | | |
| 12 | Sequence A* | 0 | X | | |
| 13 | WP_074665058 | 0 | X | | |
| 14 | WP_094397369 | X | 0 | | |

TABLE 2-continued

| SEQ ID NO: | Genbank No. | Motif III (M-X-X-N/K-P-G) | Motif I (V-D-G) | Psicose 6 phosphate 3-epimerization activity | Psicose 3-epimerization activity |
|---|---|---|---|---|---|
| 15 | WP_093231204 | 0 | | | No active*** |
| 16 | Sequence B* | 0 | | | |
| 17 | WP_082829565 | 0 | | | |
| 18 | WP_025950644 | 0 | | | |
| 19 | AEE96948 | 0 | | | |
| 20 | WP_085113038 | 0 | | | |
| 21 | WP_094046601 | 0 | | | |
| 22 | WP_059031935 | 0 | | | |
| 23 | PWH13270 | 0 | | | |
| 24 | PKM55438 | 0 | | | |
| 25 | WP_117016900 | 0 | | | |
| 26 | ON183610 | 0 | | | |

*Sequence A, B: Some sequences (4 to 10 amino acids) are inserted into the ribulose-phosphate 3-epimerase sequence.
***no active: conversion rate within 5%

Further, an enzyme having an amino acid sequence of SEQ ID NO: 20 of the present disclosure was confirmed to show remarkably low fructose production, as compared with the known psicose-6-phosphate 3-epimerase (FIG. 2).

This indicates that the presence or absence of the motif plays an important role in the allulose production yield.

Further, the sequence including SEQ ID NO: 4 and/or SEQ ID NO: 5 was confirmed to show high psicose-G-phosphate 3-epimerization activity.

Example 4: Analysis of Psicose Production Activity Through Complex Enzymatic (Multiple Enzymatic) Reaction To produce psicose from maltodextrin, glucan phosphorylase, pullulanase, 4-alpha-glucanotransferase, phosphoglucomutase, glucose-6-phosphate isomerase, psicose-6-phosphate phosphatase, and fructose-6-phosphate 3-epimerase of the present disclosure were subjected to a one-pot reaction.

Specifically, each 0.1 unit/mL of the seven kinds of enzymes was added to a solution, in which 5% (w/v) maltodextrin was added to 1 mM to 5 mM $MgCl_2$, 10 mM to 50 mM sodium phosphate (pH 7.0), and allowed to react at a temperature of 50° C. for 12 hours.

After the reaction was completed, psicose in the reaction products was analyzed by HPLC. HPLC analysis was performed using an Aminex HPX-87C (Bio-RAD) column at 80° C. using a mobile phase at a flow rate of 0.6 mL/min, and detection was performed using a refractive index detector. As a result, it was confirmed that psicose was produced from maltodextrin by way of the complex enzymatic reaction.

TABLE 3

| SEQ ID NO: | Genbank No. | Production of psicose |
|---|---|---|
| 15 | WP_093231204 | 0 |
| 16 | Sequence B** | 0 |
| 17 | WP_082829565 | 0 |
| 18 | WP_025950644 | 0 |
| 19 | AEE96948 | 0 |
| 20 | WP_085113038 | 0 |
| 21 | WP_094046601 | 0 |
| 22 | WP_059031935 | 0 |
| 23 | PWH13270 | 0 |
| 24 | PKM55438 | 0 |
| 25 | WP_117016900 | 0 |
| 26 | ON138610 | 0 |

Based on the above description, it will be understood by those skilled in the art that the present disclosure may be implemented in a different specific form without changing the technical spirit or essential characteristics thereof. In this regard, it should be understood that the above embodiment is not limitative, but illustrative in all aspects. The scope of the disclosure is defined by the appended claims rather than by the description preceding them, and therefore all changes and modifications that fall within metes and bounds of the claims, or equivalents of such metes and bounds, are therefore intended to be embraced by the claims.

Effect of the Invention

Since the ribulose-phosphate 3-epimerase of the present disclosure does not include a specific motif, it has low psicose 3-epimerization activity and has heat resistance, and thus has advantages in industrial applications such as psicose production, etc.

What is claimed is:

1. A method of producing psicose-6-phosphate, the method comprising
the step of bringing fructose-6-phosphate into contact with ribulose-phosphate 3-epimerase, a microorganism expressing the ribulose-phosphate 3-epimerase, or a culture of the microorganism such that the ribulose-phosphate 3-epimerase catalyzes the conversion of fructose-6-phosphate into psicose-6-phosphate,
wherein the ribulose-phosphate 3-epimerase includes a motif I consisting of an amino acid sequence of SEQ ID NO: 1 and a motif III consisting of an amino acid sequence of SEQ ID NO: 3, and does not include a motif II consisting of an amino acid sequence of SEQ ID NO: 2, and wherein the motifs I and III are present at a substrate and/or a metal ion binding site of the enzyme.

2. The method of claim 1, wherein the ribulose-phosphate 3-epimerase has no activity of converting psicose to fructose or 5% or less of the activity.

3. The method of claim 1, wherein the ribulose-phosphate 3-epimerase further comprises a motif consisting of an amino acid sequence of SEQ ID NO: 4 or 5.

4. The method of claim 1, wherein the ribulose-phosphate 3-epimerase includes the motif I at positions 173 to 184 from the N-terminal amino acid, or wherein the ribulose-phosphate 3-epimerase includes the motif III at positions 136 to 150 from the N-terminal amino acid.

5. The method of claim 1, wherein the ribulose-phosphate 3-epimerase has psicose-6-phosphate 3-epimerization activity at a temperature of 50° C. to 90° C.

6. The method of claim 1, wherein the ribulose-phosphate 3-epimerase is derived from any one selected from the group consisting of *Chthonomonas, Geobacillus, Mahella, Thermoanaerobacterium, Tepidanaerobacter, Ardenticatenia, Firmicutes, Aeribacillus, Epulopiscium, Thermoflavimicrobium, Chthonomonas calidirosea* T49, *Geobacillus* sp. 8, *Geobacillus thermocatenulatus, Mahella australiensis* 50-1 BON, *Thermoanaerobacterium* sp. PSU-2, *Thermoanaerobacterium thermosaccharolyticum, Tepidanaerobacter syntrophicus, Ardenticatenia bacterium, Firmicutes bacterium* HGW-Firmicutes-5, *Aeribacillus pallidus, Epulopiscium* sp. SCG-B05WGA-EpuloA1, and *Thermoflavimicrobium dichotomicum*.

7. The method of claim 1, wherein the ribulose-phosphate 3-epimerase consists of any one sequence selected from the group consisting of amino acid sequences of SEQ ID NOs: 15 to 26 and amino acid sequences having at least 26% identity to the region excluding the motifs I and III in the amino acid sequences.

8. The method of claim 1, wherein the method further comprises bringing the psicose-6-phosphate produced from the fructose-6-phosphate into contact with psicose-6-phosphate phosphatase, a microorganism expressing the psicose-6-phosphate phosphatase, or a culture of the microorganism.

9. The method of claim 8, wherein the method further comprises obtaining psicose produced from psicose-6-phosphate.

10. The method of claim 1, wherein the ribulose-phosphate 3-epimerase has psicose-6-phosphate 3-epimerization activity at a temperature of 45° C. to 70° C.

11. The method of claim 1, wherein the method is performed for 1 hour to 24 hours.

12. The method of claim 1, wherein the method is performed for 2 hours to 24 hours.

13. The method of claim 1, wherein the method is performed for 6 hours to 24 hours.

14. The method of claim 1, wherein the ribulose-phosphate 3-epimerase comprises the amino acid sequence of SEQ ID NO: 20 and amino acid sequences having at least 26% identity to the region excluding the motifs I and III in the amino acid sequences.

15. The method of claim 1, wherein the ribulose-phosphate 3-epimerase comprises any one sequence selected from the group consisting of amino acid sequences of SEQ ID NOs: 15 to 18 and amino acid sequences having at least 26% identity to the region excluding the motifs I and III in the amino acid sequences.

16. The method of claim 1, wherein the ribulose-phosphate 3-epimerase comprises any one sequence selected from the group consisting of amino acid sequences of SEQ ID NOs: 21 or 22 and amino acid sequences having at least 26% identity to the region excluding the motifs I and III in the amino acid sequences.

17. The method of claim 1, wherein the ribulose-phosphate 3-epimerase comprises any one sequence selected from the group consisting of amino acid sequences of SEQ ID NOs: 23 or 24 and amino acid sequences having at least 26% identity to the region excluding the motifs I and III in the amino acid sequences.

18. The method of claim 1, wherein the ribulose-phosphate 3-epimerase comprises any one sequence selected from the group consisting of amino acid sequences of SEQ ID NOs: 25 or 26 and amino acid sequences having at least 26% identity to the region excluding the motifs I and III in the amino acid sequences.

19. A method of producing psicose, the method comprising steps of
bringing fructose-6-phosphate into contact with ribulose-phosphate 3-epimerase, a microorganism expressing the ribulose-phosphate 3-epimerase, or a culture of the microorganism such that the ribulose-phosphate 3-epimerase catalyzes the conversion of fructose-6-phosphate into psicose-6-phosphate; and
bringing psicose-6-phosphate produced from the fructose-6-phosphate into contact with psicose-6-phosphate phosphatase, a microorganism expressing the psicose-6-phosphate phosphatase, or a culture of the microorganism,
wherein the ribulose-phosphate 3-epimerase includes a motif I consisting of an amino acid sequence of SEQ ID NO: 1 and a motif III consisting of an amino acid sequence of SEQ ID NO: 3, and does not include a motif II consisting of an amino acid sequence of SEQ ID NO: 2, and wherein the motifs I and III are present at a substrate and/or a metal ion binding site of the enzyme.

20. The method of claim 19, further comprising the step of obtaining psicose produced from psicose-6-phosphate.

\* \* \* \* \*